US010004946B2

(12) United States Patent
Ross

(10) Patent No.: US 10,004,946 B2
(45) Date of Patent: Jun. 26, 2018

(54) SYSTEM AND METHOD FOR MONITORING POWER APPLIED TO A BICYCLE

(71) Applicant: MedHab, LLC, Mansfield, TX (US)

(72) Inventor: Johnny Ross, Mansfield, TX (US)

(73) Assignee: Medhab, LLC

( * ) Notice: Subject to any disclaimer, the term of this patent is extended or adjusted under 35 U.S.C. 154(b) by 856 days.

(21) Appl. No.: 14/505,106

(22) Filed: Oct. 2, 2014

(65) Prior Publication Data

US 2015/0025816 A1    Jan. 22, 2015

Related U.S. Application Data

(63) Continuation-in-part of application No. 14/217,337, filed on Mar. 17, 2014, now Pat. No. 9,453,772, which is a continuation-in-part of application No. 13/749,665, filed on Jan. 24, 2013, now abandoned, which is a continuation-in-part of application No. (Continued)

(51) Int. Cl.
| | | |
|---|---|---|
| *G01L 1/00* | (2006.01) | |
| *A63B 24/00* | (2006.01) | |
| *G01P 7/00* | (2006.01) | |
| *A43B 3/00* | (2006.01) | |
| *A61B 5/103* | (2006.01) | |
| *A61B 5/11* | (2006.01) | |
| *A61B 5/00* | (2006.01) | |

(Continued)

(52) U.S. Cl.
CPC ........ *A63B 24/0062* (2013.01); *A43B 3/0005* (2013.01); *A43B 5/14* (2013.01); *A43B 17/00* (2013.01); *A61B 5/1038* (2013.01); *A61B 5/11* (2013.01); *A61B 5/6807* (2013.01); *G01P 7/00* (2013.01); *A61B 5/6811* (2013.01); *A61B 5/743* (2013.01); *A61B 2562/0219* (2013.01); *A61B 2562/0247* (2013.01); *A61B 2562/12* (2013.01); *A63B 2220/00* (2013.01); *A63B 2220/51* (2013.01); *Y10T 29/49128* (2015.01)

(58) Field of Classification Search
CPC . G01L 5/225; G01L 3/24; G01L 3/242; G01L 3/247; A63B 2220/51; A63B 2220/40; A63B 2220/833; A63B 24/0062; A63B 71/0619; G01D 21/00; G01P 3/22; G06F 3/011
See application file for complete search history.

(56) References Cited

U.S. PATENT DOCUMENTS 5,042,504 A  8/1991 Huberti
5,107,854 A  4/1992 Knotts et al.
(Continued)

FOREIGN PATENT DOCUMENTS

WO    WO 2012/128801    9/2012

*Primary Examiner* — Elias Desta
(74) *Attorney, Agent, or Firm* — Eric Karich; Karich & Associate

(57) ABSTRACT

A sensor system and method for monitoring power exerted by a person riding a bicycle has a pair of sensor insoles and a portable electronic device. The sensor insoles each have a plurality of force sensors, an accelerometer, and a transmitter for transmitting data from the plurality of force sensors and the accelerometer. A power measurement program operably installed in the computer memory of the portable electronic device receives the data and calculates power and other outputs based upon the data received.

8 Claims, 14 Drawing Sheets

Related U.S. Application Data

13/741,294, filed on Jan. 14, 2013, now abandoned, which is a continuation-in-part of application No. 13/070,649, filed on Mar. 24, 2011, now Pat. No. 8,384,551.

(60) Provisional application No. 61/800,981, filed on Mar. 15, 2013, provisional application No. 61/867,064, filed on Aug. 17, 2013, provisional application No. 61/889,878, filed on Oct. 11, 2013.

(51) Int. Cl.
*A43B 5/14* (2006.01)
*A43B 17/00* (2006.01)

(56) References Cited

U.S. PATENT DOCUMENTS

| | | | |
|---|---|---|---|
| 5,240,417 A * | 8/1993 | Smithson | A63B 21/00181 348/121 |
| 5,269,081 A | 12/1993 | Gray | |
| 5,323,650 A | 6/1994 | Fullen | |
| 5,357,696 A | 10/1994 | Gray | |
| 5,373,651 A | 12/1994 | Wood | |
| 5,408,873 A | 4/1995 | Schmidt et al. | |
| 5,452,269 A | 9/1995 | Cherdak | |
| 5,619,186 A | 4/1997 | Schmidt et al. | |
| 5,661,916 A | 9/1997 | Huang | |
| 5,724,265 A | 3/1998 | Hutchings | |
| 5,815,954 A | 10/1998 | Huang | |
| 5,875,571 A | 3/1999 | Huang | |
| 5,992,553 A * | 11/1999 | Morrison | B62M 6/45 180/206.2 |
| 6,122,846 A | 9/2000 | Gray | |
| 6,273,863 B1 | 8/2001 | Avni | |
| 6,356,856 B1 | 3/2002 | Damen et al. | |
| 6,418,797 B1 | 7/2002 | Ambrosina | |
| 6,578,291 B2 | 6/2003 | Hirsch et al. | |
| 7,277,021 B2 | 10/2007 | Beebe et al. | |
| 8,011,242 B2 * | 9/2011 | O'Neill | G01L 3/242 73/379.01 |
| 2006/0248965 A1 * | 11/2006 | Wyatt | A61B 5/0002 73/862.391 |
| 2007/0049853 A1 | 3/2007 | Adams et al. | |
| 2007/0170688 A1 | 7/2007 | Watson | |
| 2007/0245835 A1 * | 10/2007 | Hauschildt | A61B 5/221 73/862.391 |
| 2007/0245838 A1 * | 10/2007 | Rieberer | E21B 21/065 73/863.23 |
| 2011/0087446 A1 | 4/2011 | Redmond et al. | |

\* cited by examiner

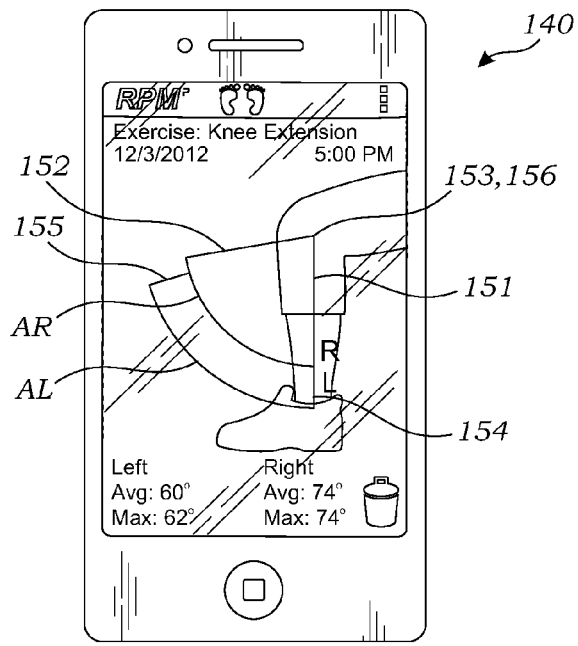
*Fig. 7*
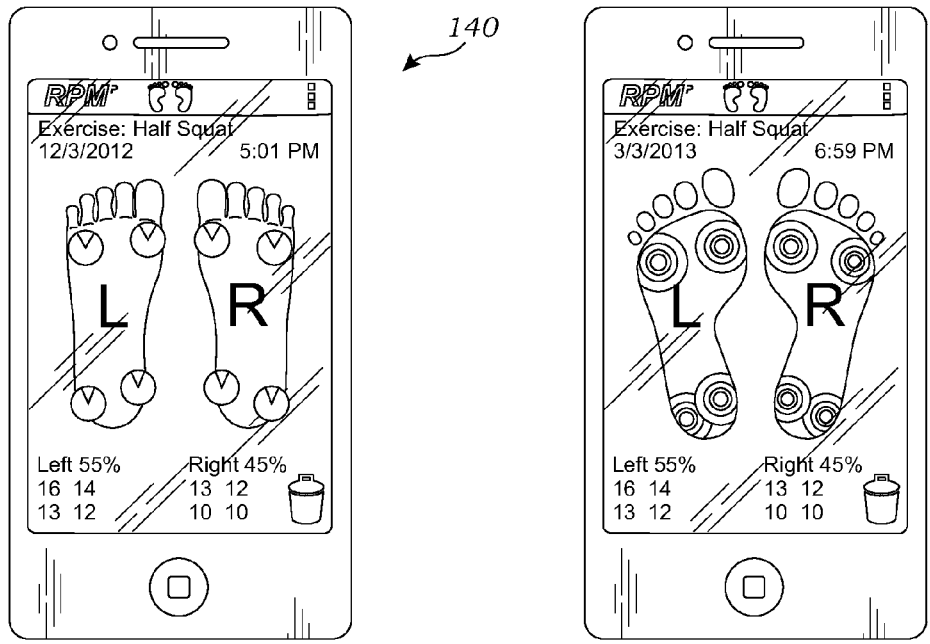
*Fig. 8*        *Fig. 9*

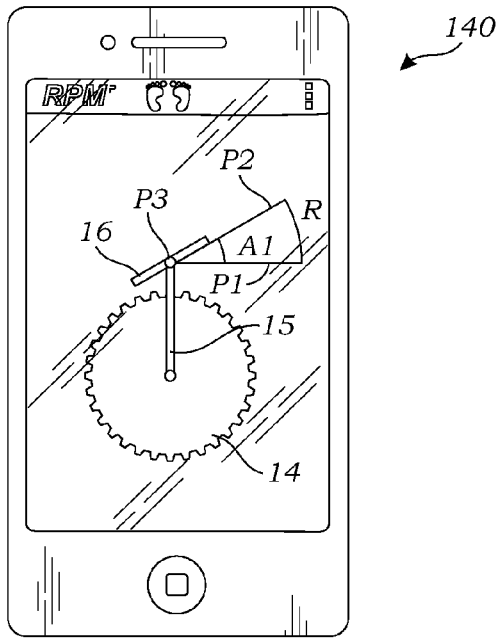
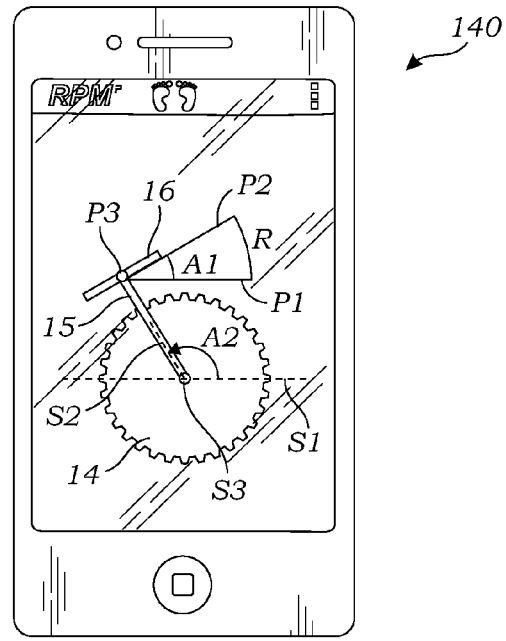
Fig. 10      Fig. 11
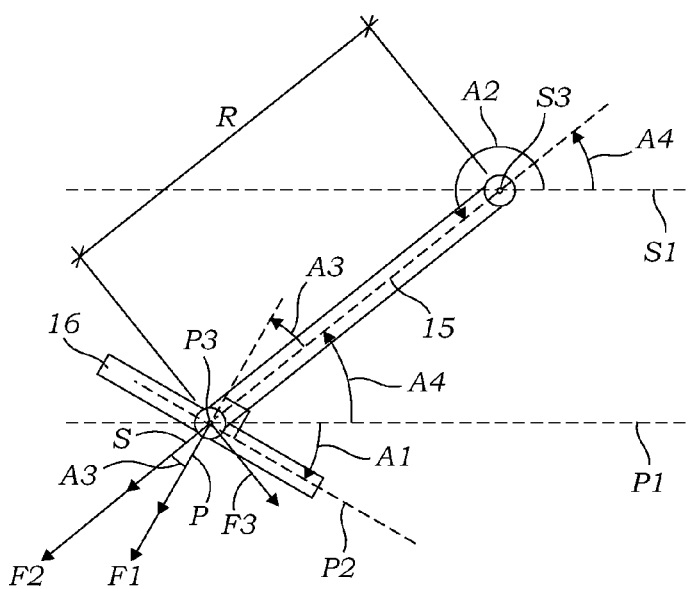
Fig. 12

SYSTEM AND METHOD FOR MONITORING POWER APPLIED TO A BICYCLE

CROSS-REFERENCE TO RELATED APPLICATIONS

This application for a utility patent is a continuation-in-part of the following previously filed utility patent applications: application Ser. No. 14/217,337, filed Mar. 17, 2014; application Ser. No. 13/749,665, filed Jan. 24, 2013; application Ser. No. 13/741,294, filed Jan. 14, 2013; and application Ser. No. 13/070,649, now U.S. Pat. No. 8,384,551, filed Mar. 24, 2011.

This application for a utility patent also claims the benefit of the following U.S. Provisional Application Nos. 61/800,981, filed Mar. 15, 2013; 61/867,064, filed Aug. 17, 2013; and 61/889,878, filed Oct. 11, 2013.

BACKGROUND OF THE INVENTION

Field of the Invention

This invention relates generally to sensor devices, and more particularly to a shoe-mounted sensor device for monitoring the movements of a person's feet, and the forces exerted upon the user's foot, to determine power exerted by the person.

Description of Related Art

Various devices have been developed for measuring power and related metrics exerted by a user on a bicycle. Typical systems utilize strain gauges and the like mounted on suitable components of the bicycle (e.g., pedals, crank arms, chains, hubs, etc.).

One such system is disclosed in Ambrosina et al., U.S. Pat. No. 6,418,797, which teaches a torque measurement system incorporated into the hub of a bicycle. A similar system is shown in Watson, U.S. 2007/0170688, which teaches a hub assembly that includes strain gauges for measuring torque and angular velocity. Power and related metrics are then displayed on a computer mounted on the handlebars of the bicycle. These references are incorporated by reference in full.

There are no devices known in the art that determine power while riding a bicycle, which are mounted in the shoes of the user.

There are various devices in the prior art that teach sensor devices for measuring force on a user's foot, usually for the purposes of assisting in rehabilitation of a user's leg following an injury, surgery, or similar situation.

Knotts et al., U.S. Pat. No. 5,107,854, teaches a slipper that includes a fluid chamber that enables weight sensing by a load monitor. When not enough weight is applied, or when too much weight is applied, a beeping sound is emitted to guide the patient in rehabilitating an injured leg.

Huberti, U.S. Pat. No. 5,042,504, teaches an insertable sole that includes plates having force sensors for determining a load placed upon the sole by a user. An amplifier and AC/DC converter generate a force signal that is received by a processor for generating audible and visual feedback via a piezo-beeper and display screen.

Gray, U.S. Pat. No. 5,269,081, teaches a force monitoring shoe that includes a spring, a sensor for sensing force applied to the spring, and a feedback mechanism that may include a beeper, flashing LEDs, a shocking element, vibrational (tactile) feedback.

Gray, U.S. Pat. No. 5,357,696, teaches a force monitoring shoe similar to the '081 patent, utilizing a force monitoring device to measure force exerted on the shoe, warn the patient (e.g., a beeper) if predetermined force levels are exceeded, and collect the accumulated data in a data gathering device. The force sensor may be a resistive sensor pad, and the patient alerting elements may include a wireless transmitter that transmits a signal to a separate unit that vibrates in response to exceeding recommended forces. The data gathering device may be a recorder, or a receiver in a doctor's office.

Schmidt et al., U.S. Pat. No. 5,619,186, teaches a rehabilitation device that measures force exerted on a sensor in a shoe for the purposes of guiding a patient in placing the correct amount of weight on an injured leg.

Schmidt et al., U.S. Pat. No. 5,408,873, teaches a similar foot force sensor that includes a special insole made of layers of relatively thin, planar, flexible dielectric material. Electrical contacts are interposed between the layers for sensing force.

Avni et al, U.S. Pat. No. 6,273,863, teaches a rehabilitation device that measures force exerted on a sensor in a shoe for the purposes of guiding a patient in placing the correct amount of weight on an injured leg.

Fullen et al., U.S. Pat. No. 5,323,650, teaches a rehabilitation device that includes a force sensor array adapted to be positioned in a shoe, a cable for connecting the force sensor array with an electronic circuit module that includes a CPU, RAM, ROM, and scanning circuitry for continuously electronically scanning the sensor array to determine instant force sensed by the sensors.

Gray, U.S. Pat. No. 6,122,846, teaches a force monitoring shoe similar to the other Gray patents described above. The shoe includes two semi-rigid plates, with a force sensor positioned therebetween. The force signals generated are transmitted via wireless to a reporting device that is separate from the shoe. The reporting device not only displays the readings, it may also be used to transmit the data to a remote computer for storage and analysis.

Beebe et al., U.S. Pat. No. 7,277,021, teaches a device for determining the wear of a sole of a shoe, to determine when the shoe is worn out and needs to be replaced. A control circuit connectable to first and second sensors compares the difference between the first and second signals to a threshold and generates an alert signal in response to the difference between the first and second signal meeting the threshold, thereby indicating that the shoe needs to be replaced, at which point an LED is illuminated.

There are various sensor devices that include accelerometers for various purposes. For example, Hirsch et al., U.S. Pat. No. 6,578,291, teaches a shoe having a built-in electronic wear indicator device that includes an accelerometer for measuring foot movement.

Damen et al., U.S. Pat. No. 6,356,856, teaches a system built into a shoe or measuring the speed of a person while running or walking. An acceleration sensor measures the acceleration in the forward direction and provides an acceleration signal which is amplified and subsequently sampled by analog to digital converter. The digital signal is processed by a microprocessor which executes an algorithm that determines the stride length and the stride duration from the digitized acceleration signal and calculates the speed and the distance traversed. The information thus obtained is transmitted by an RF transceiver to a watch or other device which includes a display which can be viewed by the runner or walker. The speed and distance traversed is displayed on the display, along with other useful information, such as average speed, maximum speed, total distance traversed, calories expended, and heart beat. Similar shoes are also shown in Huang, U.S. Pat. No. 5,875,571, Huang, U.S. Pat. No. 5,815,954, Hutchings, U.S. Pat. No. 5,724,265, and Huang, U.S. Pat. No. 5,661,916.

Cherdak, U.S. Pat. No. 5,452,269, teaches an athletic shoe which includes a timing device for measuring the amount of time the athletic shoe is off the ground and in air. The athletic shoe includes a notification device which can be operatively coupled to the timing device for notifying a wearer of the amount of time the athletic shoe is off the ground and in the air.

Wood, U.S. Pat. No. 5,373,651, teaches footwear adapted to measure the number and the force of steps that have been taken by the user during a predetermined interval. The wearer can subsequently transfer the step information into a computer for further analysis via an inductively coupled data link between the footwear and the computer.

SUMMARY OF THE INVENTION

The present invention teaches certain benefits in construction and use which give rise to the objectives described below.

The present invention provides a sensor system and method for monitoring power exerted by a person riding a bicycle. The system includes a pair of sensor insoles and a portable electronic device. The sensor insoles each include a substrate layer is shaped to be worn adjacent the underside of the foot, such as in the person's shoes or other form of footwear. The substrate layer has a plurality of force sensors, an accelerometer, and a transmitter for transmitting data from the plurality of force sensors and the accelerometer. The portable electronic device has a computer processor and a computer memory for receiving the data transmitted from the transmitter of the sensor insoles, and a computer display. A power measurement program operably installed in the computer memory of the portable electronic device performs the following steps: receiving the data from the accelerometer regarding movement of the sensor insoles; receiving the data from the force sensors to determine a force exerted by the person again the pedals via the substrate layer; and calculating power and other outputs based upon the data received.

A primary objective of the present invention is to provide a sensor system having advantages not taught by the prior art.

Another objective is to provide a sensor system that enables the calculation of power exerted while riding a bicycle, without requiring any changes to the bicycle, or installation of sensors in or on the pedals of the bicycle.

Another objective is to provide a method of calculating power using the sensor system described herein, or an equivalent system, that is fast, easy, and accurate.

Another objective is to provide a sensor system that is able to output various forms of data regarding the person's activities on the bicycle, such as cadence, average power, average maximum power, and other data, so that the person can receive, in real time, information to assist him or her in accomplishing his or her objectives during the ride.

Another objective is to provide a sensor system that is able to assist the person in his or her training, to optimize his or her speed and endurance.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The advantages and features of the present invention will become better understood with reference to the following more detailed description taken in conjunction with the accompanying drawings in which:

FIG. 7 is a perspective view of the portable electronic device having the monitoring app installed thereupon for monitoring the angular sweep of a user's legs when performing knee extensions;

FIG. 8 is a perspective view of the portable electronic device having the monitoring app installed thereupon for monitoring the forces measured by force sensors in the sensor insoles and illustrating the data in the form of a pie graph;

FIG. 9 is a perspective view of the portable electronic device having the monitoring app installed thereupon for monitoring the forces measured by the force sensors in the sensor insoles and illustrating the data in the form of a contour plot;

FIG. 10 is a perspective view of the portable electronic device having the monitoring app installed thereupon for monitoring the angle of a user's foot while pedaling a bicycle;

FIG. 11 is a perspective view of the portable electronic device monitoring the angle of a user's foot while the pedal is moved to a different position than that shown in FIG. 10;

FIG. 12 illustrates the geometry of a pedal-crankarm system in relation to a force applied by the bicyclist;

DETAILED DESCRIPTION OF THE INVENTION

Figure 1:
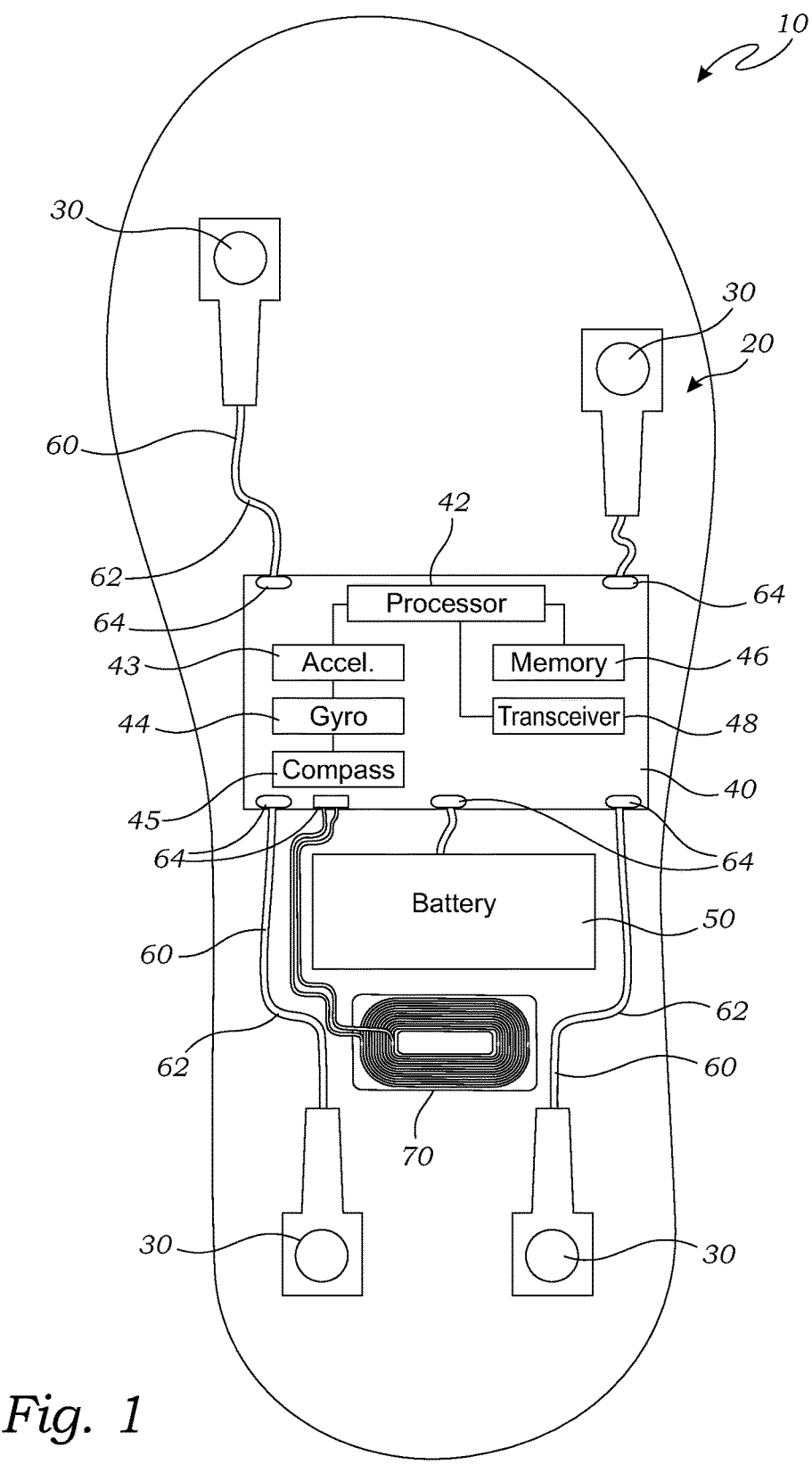
FIG. 1 is a block diagram of a sensor insole, according to one embodiment of the present invention.

FIG. 1 is a block diagram of a sensor insole 10, according to one embodiment of the present invention. A felt layer, discussed below, is removed in this view to more clearly show a sensor assembly 20 that is located within the sensor insole 10.

As illustrated in FIG. 1, the sensor insole 10 is shaped and adapted to fit within a shoe of a user (not shown), or otherwise positioned against the underside of the foot of the user. The sensor assembly 20 is mounted on the sensor insole 10 for monitoring various forces and conditions of the sensor insole 10, in this embodiment the sensor assembly 20 includes force sensors 30. In the embodiment of FIG. 1, the sensor insole 10 may include a printed circuit board ("PCB") 40 having (or being operably attached to a computer processor 42, a computer memory 46, a battery 50, and the force sensors 30. The force sensors 30 may be any form of sensors useful for sensing force that are known in the art. While four of the force sensors 30 are illustrated, in different embodiments other numbers of the force sensors 30 may be used, depending upon the requirements of the user.

The force sensors 30 are adapted to send signals to the processor 42, transferring the values of the properties sensed by the force sensors 30 individually. Each of the plurality of force sensors 30 may be operably connected to the processor 42 by electrical connectors 60, in this case wires, or any other operative connection known in the art.

In this embodiment, the wires 60 may be attached to the PCB 40 via soldering; however, the wires 60 may be attached using any techniques or attachment mechanisms known in the art. The solder joints may also be covered with a protective layer, to strengthen the connection to withstand the stresses and strains placed upon the wires 60. This is further discussed in the descriptions of FIGS. 15-17.

The wires 60 may be positioned in an S-curve configuration 62 between the force sensor 30 and the PCB 40. The S-curve configuration 62 provides strain relief during use, so that the electrical connection is not broken during use. For purposes of this application, the term "S-curve configuration" is defined to include any configuration in which the wires 60 are bent in places, so that the wires 60 are long enough to accommodate forces against the various components while in use without breaking any solder joints.

The processor 42 and the memory 46 may be any form of processor or processors, memory chip(s) or devices, microcontroller(s), and/or any other devices known in the art.

The battery 50 supplies power to the processor 42 and the plurality of force sensors 30. The battery 50 may be rechargeable which can be charged by an external power source, or in alternative embodiments it may be replaceable. The sensor assembly 20 may further include an inductive charging coil 70 which may be operably mounted adjacent the battery 50 and/or the PCB 40. The inductive charging coil 70 is used to charge the battery 50 by using an external inductive charger (not shown). Other devices or systems known in the art for supplying power may also be utilized, including various forms of charging the battery 50, and/or generating power directly using piezoelectric, solar, or other devices.

The sensor assembly 20 may further include one or more accelerometers 43, one or more micro-electro-mechanical-systems "MEMS" gyroscopes 44, and/or a compass 45 to record movement, rotation, and direction data respectively and supply the data to the processor 42. The accelerometer 43, the gyroscope 44, and the compass 45 may be operably connected to the processor 42 via being operably mounted on the PCB 40, or they may be mounted elsewhere and connected via the wires 60.

In the present embodiment, the force sensors 30 are piezoresistance based, meaning that the resistance of the circuit in which they have been integrated changes in response to the applied force. Other methods known to those skilled in the art may also be used to provide a force sensing mechanism. The applied force may then be determined by incorporating the force sensors 30 in a voltage divider, whereby the voltage across the force sensor 30 would change in response to the applied force, an RC circuit whereby the time constant would change in response to the applied force, or integrating an Ohmmeter to measure the resistance directly, or other methods of reading the applied force known to those skilled in the art. If a force measurement is desired instead, the known area of measurement allows that to be determined directly. The force sensors 30 have an upper limit to the force they may measure and still be accurate or without breaking. Using the plurality of force sensors 30 as shown in the present embodiment allows total force to be shared amongst the force sensors 30 and to measure the force distribution in the user's foot. The use of small sensors allows the force to be sampled over a smaller fraction of the surface area of the foot, giving a proportionally smaller force.

The force sensors 30, in the present embodiment, have a high sampling rate, up to 200 kHz, which is far beyond what would normally be needed for an activity like walking, but may be desirable when one wishes to analyze more impulsive forces, such as those due to running or kicking. Variations in sampling rate and duration are described in a later discussion of possible applications possible of the present invention, but may be adjusted by the user. A typical sampling rate for activities such as walking or other slow motions may be around 10 Hz. As mentioned before, temperature sensors (not shown) may also be incorporated into the sensor assembly 20 for providing temperature data. This is important as the force sensor 30 may also be weakly temperature dependent and therefore changes in temperature may need to be corrected for.

The integrated motion tracker provides data on the linear acceleration in three linear dimensions, roll, pitch, yaw, position, bearing, and heading. These nine coordinate measurements provide a complete description of the motion and position of the user's foot. In the present embodiment, the motion tracker combines the accelerometer 43, the gyroscope 44, and the compass 45. Other motion trackers may also be used by those skilled in the art and are within the scope of the present invention.

The processor 42 may also include the memory 46 to store data collected by the plurality of sensors 30, and a transceiver 48 to transmit and receive signals for communication between the processor 42 and external computing devices enabled to send and receive the signals. The processor 42, the memory 46 and the transceiver 48 may all be mounted on the PCB 40, or in other suitable locations as determined by one skilled in the art.

The sensor insole 10 may be used in conjunction with a shoe (not shown), including any form of sneaker, slipper, or any other footwear known in the art. As a person wearing the shoe walks, force is exerted on the sensor insole 10, and data from the force sensors 30 can be collected. The data collected by the processor 42 from different force sensors 30 may be used in a variety of ways. The sensor assembly 20 may use the transceiver 48 to connect and transfer data from the sensor assembly 20 to a local and/or remote computer (not shown). The data may be transmitted by the transceiver 48 by any number of methods known to those skilled in the art, however, in particular, the data may be transferred in packets or bundles, containing multiple bytes or bits of information. The bundling of the data may be performed according to those skilled in the art for optimizing the data transfer rate between the sensor insole 10 and any remote receiver. Alternatively in another embodiment, the data may be reported via a reporting device worn by the user, attached to the shoe, located nearby, or located remotely. In another embodiment, the data may also be used to compare with a threshold value and take a predefined action based on the comparison. The data may be received, collected, reviewed, and utilized using different forms of computer devices.

Figure 2:
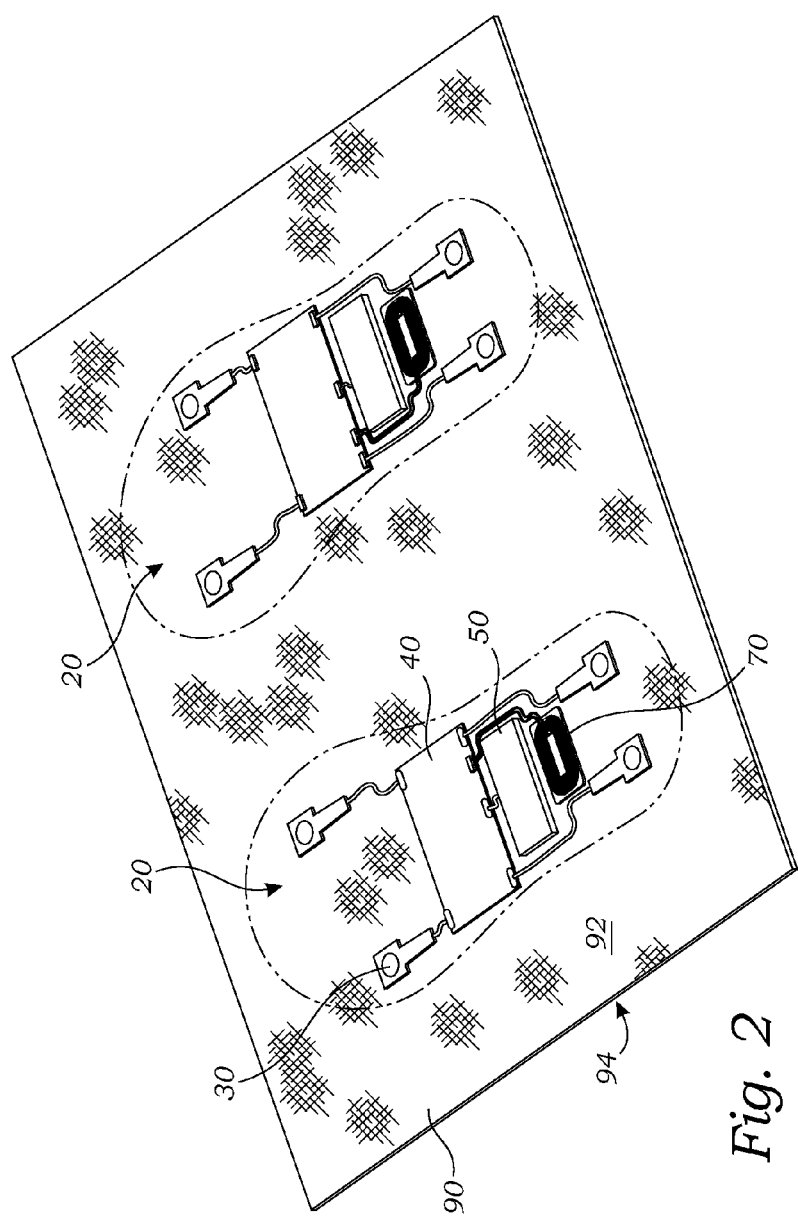
FIG. 2 is a perspective view of a felt layer on which is mounted two sensor assemblies.

FIG. 2 is a perspective view of a felt layer 90 on which is mounted two of the sensor assemblies 20 of FIG. 1. As illustrated in FIG. 2, the felt layer 90 has a top surface 92 and a bottom surface 94. The felt layer 90 may be large enough for one sensor assembly 20; or alternatively, it may be large enough for a pair of the sensor assemblies 20, as illustrated, or it may be large enough for a larger number of the sensor assemblies 20, depending upon the manufacturing requirements of the user. The felt layer 90 should neither be very thick, such that the force sensors 30 are not able to sense the wearer's foot properties correctly, nor be very thin so that the sensor assembly 20 causes pain or discomfort to the user's foot.

The term "felt layer" is hereby defined to include one or more layers of woven and/or nonwoven material (which may be produced by, e.g., matting, condensing and pressing woolen fibers bonded together by chemical, mechanical, heat or solvent treatment), and to also include one or more layers any form of cloth, flexible synthetic material, and any other layer of material that is suitable for insertion into a shoe consistent with the description of the present invention. The scope of this term should be broadly construed to include any material or materials that may be devised by one skilled in the art for this purpose. The felt layer 90 should be flexible enough to bend as a person wearing the shoe walks, without offering any significant resistance to the bending such that no discomfort is felt by the wearer while walking.

The sensor assemblies 20 may be mounted on the felt layer 90, or it may just be placed thereupon. In one embodiment, the sensor assembly 20 may be attached to the felt layer 90 using an adhesive (not shown) or a suitable tacky substance. The purpose of attaching the sensor assembly 20 with the felt layer 90 is to retain the location of the force sensors 30 and other components of the sensor assembly 20, such as the PCB 40, the battery 50, and the inductive charging coil 70, during the molding process. Any alternative method which serves the purpose of properly positioning the sensor assembly 20 may also be used and may not require any bonding or direct attachment of the sensor assembly 20 to the felt layer 50, in an alternative embodiment.

Figure 3:
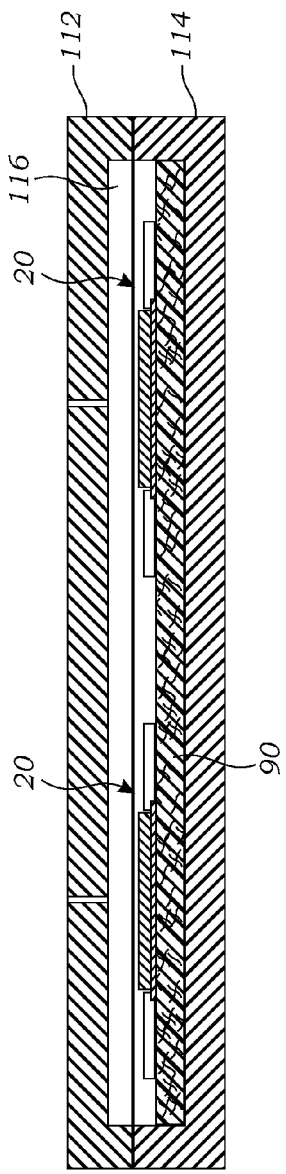
FIG. 3 is a sectional view of a mold in which the felt layer and the sensor assemblies are placed.

FIG. 3 is a sectional view of a mold 110 in which the felt layer 90 and the sensor assemblies 20 are placed. As illustrated in FIG. 3, the mold 110 may include a top portion 112 and a bottom portion 114 that close together to form a planar internal cavity 116; however, any suitable construction functional as described may be used, according to the knowledge of one skilled in the art. The mold 110 further includes components (not shown) to supply a suitable resilient material (e.g., urethane foam, rubber, or any suitable resilient material known in the art) to form a resilient sheet on top of the felt layer 90 inside the internal cavity 116. The mold 110 may include conduits 117 for injecting the urethane foam and to allow air and gases to escape from the closed mold 110.

Figure 4:
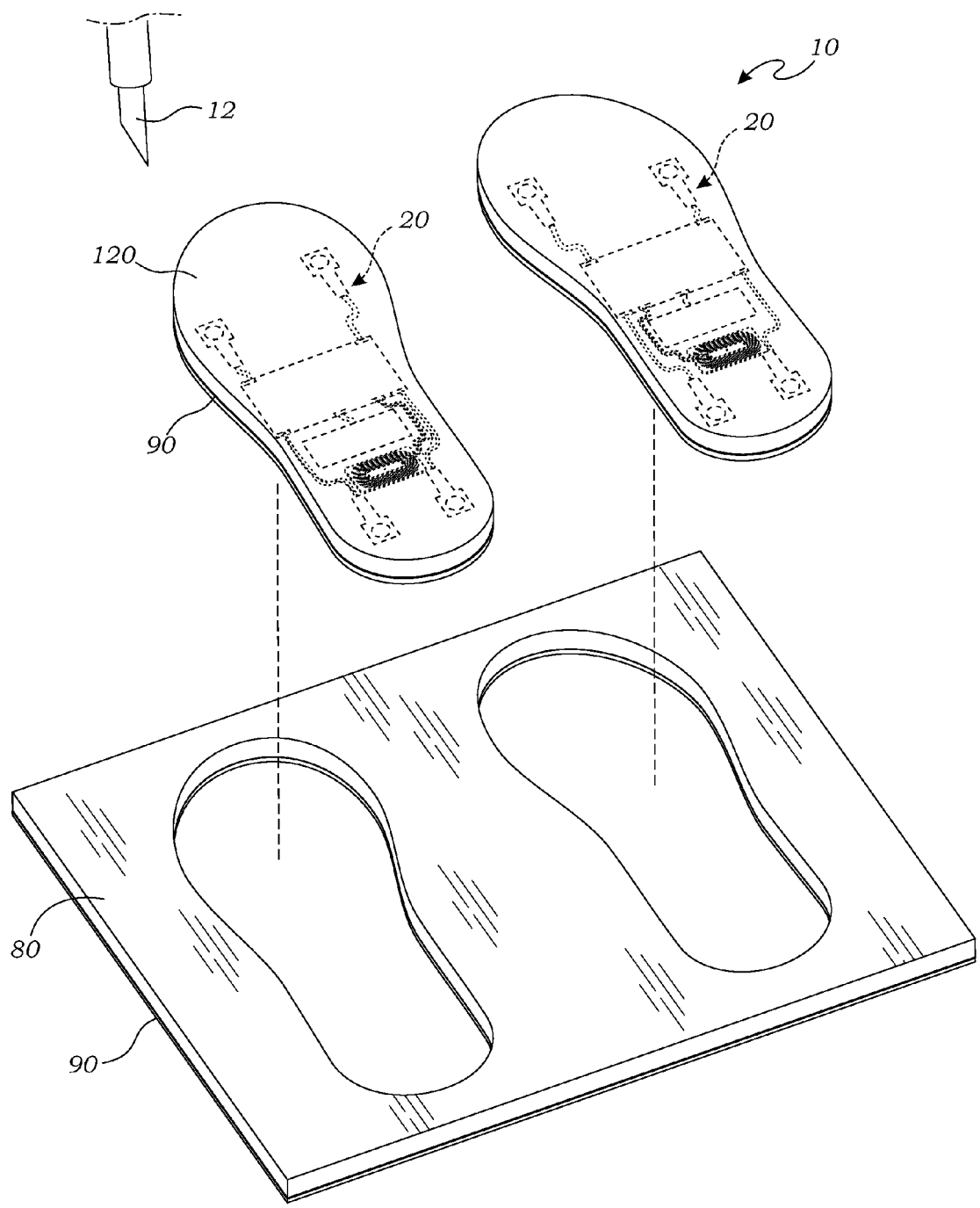
FIG. 4 is an exploded perspective view of a sensor sheet removed from the mold once urethane has been injected to form a urethane layer, illustrating the sensor insoles being cut from the sensor sheet.

FIG. 4 is an exploded perspective view of a sensor sheet 80 removed from the mold 110 of FIG. 3 once urethane foam has been injected to form a urethane layer 120 over the felt layer 90. As illustrated in FIG. 4, the sensor sheet 80 includes the felt layer 90 and the urethane layer 120 over the felt layer 90, with the sensor assembly 20 sandwiched between the felt layer 90 and the urethane layer 120.

FIG. 4 also illustrates the sensor insoles 10 being cut from the sensor sheet 80 via a cutting element 12. The cutting element 12 may be any form of cutting device, blade, die, or similar device. The cutting element 12 may be used to cut the sensor sheet 80 around the sensor assembly 20 to form a generally foot-shaped perimeter 100 and thereby forming the sensor insole 10 with the urethane layer 120 surrounding the sensor assembly 20 and over the cut out felt layer 90. The foot-shaped perimeter 100 is not necessarily a particular shape, as long as it may be placed into a shoe or other device to be worn by the user. There may be different sizes of the sensor insoles 10 depending on the size of shoes where the sensor insoles 10 would be used. In one embodiment of the present invention, only five sizes of the sensor insoles 10 are made and all other sizes will be cut or otherwise adapted from these original five sizes.

Figure 5:
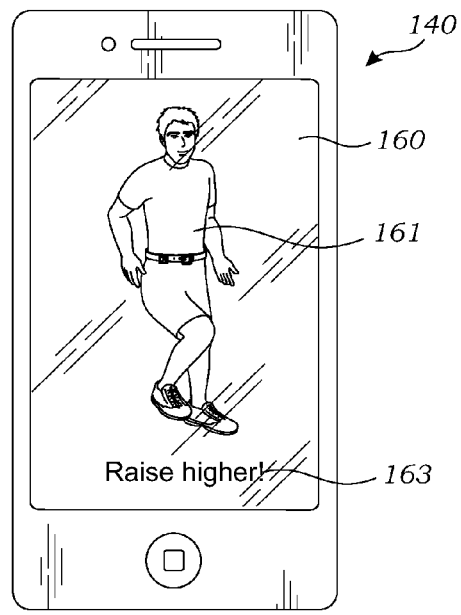
FIG. 5 is a perspective view of a portable electronic device having a monitoring app installed thereupon for monitoring the movement of a user, and for illustrating the movements of the user on a display of the portable electronic device.
Figure 6:
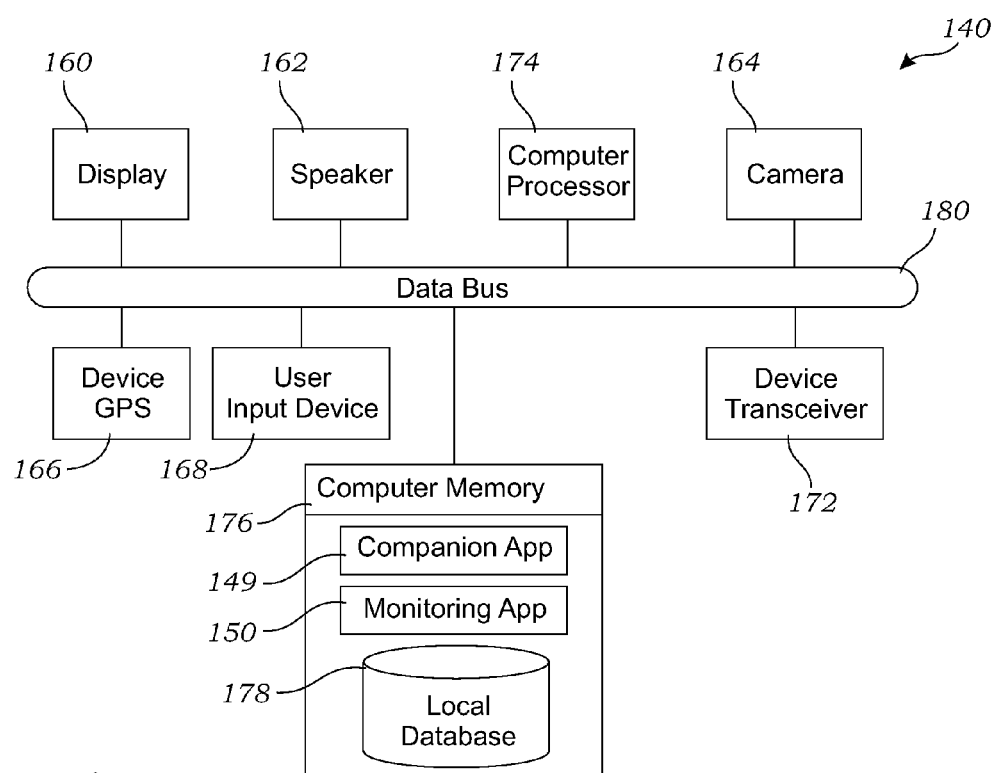
FIG. 6 is a block diagram of the operable components of the portable electronic device of FIG. 5.

FIG. 5 is a perspective view of one embodiment of a portable electronic device 140 that may be utilized with the sensor insoles. As illustrated in FIGS. 5-6, the portable electronic device 140 of this embodiment is a smart phone that includes a monitoring app 150 (discussed in FIG. 6, below) installed thereupon. The application, or "app," is a computer program that may be downloaded and installed using methods known in the art. The app enables the user to monitor their movement as detected and analyzed by the sensor insoles 10, as illustrated in FIG. 5, and to communicate with the sensor insoles 10 as described in greater detail below to aid in executing proper physical motions. In the discussion of FIGS. 5-6, we will begin with a description of the components of the portable electronic device 140, as they relate to the present invention. Then we will discuss in greater detail the functionality of the monitoring app 150, in one example, an embodiment used for physical therapy, and in another example, an embodiment used for the training of a bicyclist.

As illustrated in FIG. 5, the monitoring app 150 also monitors a person performing a physical activity, and displays the physical activity in real time (defined to include near-real time, with a slight delay for computer processing, transmission, etc.). The sensor system 300, shown in FIG. 13, includes the sensor insoles 10 and the portable electronic device 140, as discussed above and below in more detail.

In the embodiment of FIG. 5, the monitoring app 150 (of FIG. 6) operably installed on the portable electronic device 140 performs multiple steps. First, a digital model 161 of the person is generated, and the digital model 161 is displayed on the computer display 160 of the portable electronic device 140. Movement of the digital model 161 is displayed, in real time, based upon the data received from the sensor insoles 10 (of FIG. 1), so that the digital model 161 of the person approximates the movement of the person performing the physical activity.

This enables the user to watch himself/herself performing the exercises, to better determine whether they are being performed correctly. The display may also be transmitted to other computer devices, such as a doctor, trainer, caretaker, etc., so that they may monitor the activities and take corrective action if required.

The movement of the digital model 161 may also be compared with a preferred movement model of the monitoring app 150 (of FIG. 6), to determine if the actual movement of the person approximates the preferred movement model, or if correction is needed. Communication with the person, in real time, with corrective instructions 163 may be provided when correction is needed. Corrective instructions 163 may include audio, text, video (e.g., video of the exercise being correctly performed), and/or any other medium desired to assist the user in performing the exercises (or other activities) correctly.

The system may also provide a script that outlines exactly how the user should perform the exercises. For examples countdowns, instructions (e.g., raise leg, lower leg, etc.), which are synchronized with the movements in the video. In this manner, the user is able to perform the exercises correctly, and receive both instruction and correction, without the requirement of having a personal trainer, which can be expensive. The system is therefore able to deliver superior training, at relatively lower costs, than are available in the prior art.

FIG. 6 is a block diagram of the operable components of the portable electronic device 140 of FIG. 5. As illustrated in FIG. 12, the portable electronic device 140 may include various electronic components known in the art for this type of device. In this embodiment, the portable electronic device 140 may include a device display 160, a speaker 162, a camera 164, a device global positioning system ("GPS"), a user input device 168 (e.g., touch screen, keyboard, microphone, and/or other form of input device known in the art), a user output device 170 (such as earbuds, external speakers, and/or other form of output device known in the art), a device transceiver 172 for wireless communication, a computer processor 174, a computer memory 176, the monitoring app 150 operably installed in the computer memory 176, a local database 178 also installed in the computer memory 176, and a data bus 180 interconnecting the aforementioned components. For purposes of this application, the term "transceiver" is defined to include any form of transmitter and/or receiver known in the art, for cellular, WIFI, radio, and/or other form of wireless (or wired) communication known in the art. Obviously, these elements may vary, or may include alternatives known in the art, and such alternative embodiments should be considered within the scope of the claimed invention.

As shown in FIG. 6, the speaker 162, typically integrated into the portable electronic device 140, though the speaker 162 may also be an external speaker, and may give the user audio feedback and instructions during use. The speaker 162 may be any sort of speaker, known by those skilled in the art, capable of transforming electrical signals to auditory output.

Another synergistic use of the monitoring app 150 with common portable electronic devices 140 is that the monitoring app 150 may be continuously calibrated by using the camera 164 of the portable electronic device 140 and common motion capture software. In this instance, if the motion capture determined that both the user's feet were on the ground, but for some reason the monitoring app 150 reported that the user's feet were not at the same level, the position of the user's feet in the monitoring app 150 could be reset to the correct value. The same calibration technique used for position may also be used for the user's velocity and acceleration.

The integration of the device GPS 166 and the sensor insoles 10 provides several benefits. First, it may be another potential method of calibration. For example, if the horizontal motion of the sensors (specifically the accelerometer 43 and the compass 45) have determined that user has traveled a certain distance, agreement can be checked with the device GPS 166 and changes can be made to the data or real-time acquisition programs. The onboard device GPS 166 also increases the safety of the user. If the user was undergoing a strenuous activity and suddenly, and/or for an extended period of time, stopped, the monitoring app 150 may determine that a problem has occurred. The monitoring app 150 could then alert the authorities or others and provide the user's location.

There are many types of user input devices 168 that may be combined for use with the present invention. One type may be the touch-screen capability present in modern smartphones. Here, the user could adjust settings, program routines, select exercises, etc. Various user input devices 168 which may be integrated with present invention, for interfacing with the monitoring app 150 or the sensor insoles 10, should be considered equivalent and within the scope thereof.

The user output devices 170 may be speakers, earbuds, external connections to computers, etc. The user output device 170 is a key component of providing feedback to the user and/or others who may be monitoring the user and is discussed in greater detail below. Various user output devices 170 may be integrated with present invention and should be considered equivalent and within the scope thereof.

The device transceiver 172 may be an integrated wireless transmitter/receiver combination, though a wired connection may be possible or desired in some instances. The device transceiver 172 may be used to communicate with the transceiver 48 on the sensor insole 10, and/or other computers or monitoring devices. Such transceivers are known to those skilled in the art and their equivalents should be considered within the scope of the present invention.

The local database 178 may be included for receiving and storing data temporarily, such as medical programs, therapy routines, logs from earlier use, and information about the user; however, this is not required, and all data may be retained in another location if desired.

The above components may be interconnected via the data bus 180, which is a generic term for a conduit of information or electronic signals. There are many possible implementations of the data bus 180 by those skilled in the art, and such implementations should be considered equivalent and within the scope of the present invention.

As illustrated in FIG. 6, the computer memory 176 of the portable electronic device 140 may be used to extend the utility of the portable electronic device 140. In this case, the computer memory of the portable electronic device 140 receives the monitoring app 150 and/or an internet browser for browsing web pages that may include additional medical or training programs. Additional programs may also be included, such as medical diagnostic programs, exercise routines, therapy routines, training programs, and others, some of which are discussed in greater detail below.

We begin a discussion of alternate embodiments of the present invention, by introducing an embodiment where the monitoring app 150 verifies connectivity with the transceiver 48 of the sensor insole 10 and the device transceiver 172. In this embodiment, the monitoring app 150 continually monitors the acquisition of data. Should data acquisition be interrupted, the monitoring app 150 will make a predetermined number of attempts, three for example, to regain connectivity. Should this fail, an alarm or other visual or audio cue will be produced, alerting the user to move the portable electronic device 140 closer to the sensor insole 10 in order to regain the data connection.

In the embodiment of FIGS. 5 and 7-11, the monitoring app 150 may be used to generate a graphical user interface on the device display 160 of the portable electronic device 140, as illustrated in FIG. 5, to enable the user to interact with the monitoring app 150. In this embodiment, the graphical user interface may be used to show the user the position of their body, in two or three dimensions, while they are performing the actions required by the instruction program. Also, such instruction may be in the form of audio commands from the speaker 162, visual cues on the monitor of the portable electronic device 140, beeping or other audio cues from the speaker 162 that would indicate pacing or other information, or vibration of the portable electronic device 140. The information given to the user by the monitoring app 150 need not be just instruction, but could also indicate when to start or stop an activity, audio or visual feedback of the results of a completed activity, information on suggested future activities or programs to utilize, or trends of a user's progress in performing various activities.

Using walking as one example, the sensors (the accelerometer 43, the gyroscope 44, and the compass 45) determine the acceleration, velocity, and position of each foot. With this information, the monitoring app 150 may guide the user as they perform the activity, and reconstruct their motion as it is saved in the computer memory 176. Because the force sensors 30 are located in several places on each foot, the alignment of the foot may be determined. The force sensors 30 may determine if the user is stepping too hard or soft, fast or slow, if their rhythm is correct, if there is a systematic drift during the course of the activity, and more. The monitoring app 150 may also provide feedback and encouragement to the user, telling them how to better perform the activity, giving them the time remaining, or coaxing them to continue even if the monitoring app 150 determines they are becoming fatigued.

In physical therapy it is just as important to not perform an activity incorrectly as it is to perform it correctly. Learning an incorrect way to move may slow the healing process, or even further injure the user. By monitoring the user's motions, the monitoring app 150 can instruct the user to stop if they are performing an activity too wrong, and if the problem cannot be corrected by the feedback provided, to seek the assistance of a medical practitioner before resuming exercises.

In a related embodiment, a companion app 149 may be installed on another instance of the portable electronic device 140, for providing a convenient way of monitoring a patient or user who is using the monitoring app 150, for example a doctor or nurse with the companion app 149 installed on a mobile device, such as a cell phone, laptop computer, tablet computer, etc. The companion app 149 may include the following functionality: the ability to report notifications of the exercise status and sensor insole data, as with the monitoring app 150, the ability to receive text, SMS, or other types of instant messaging or alerts to inform the user of the companion app 150 that the user of the monitoring app 150 has missed an exercise or other scheduled activity, the ability to video the patient performing exercises, with the videos able to be sent to health care providers or others, and the ability to receive notifications from providers or others requesting videos or other data from the patient, practitioner, trainer, or any user of the companion app 149 or monitoring app 150. Other functions of the companion app 149 and their modes of implementation may be added or modified by those skilled in the art, and should be considered equivalent and within the scope of the present invention.

A related feature of the present invention is that it enables, both in real-time and over longer timespans, the user to engage in activities that encourage bilateral equivalence. When an activity is performed, it is often important to not favor one side over another. If a user desires to treat both sides, it is often natural that one side is 'better' at an exercise than the other, either due to handedness or prior physical condition. For instance, if one side is stronger than the other, the force sensors 30 may detect greater force applied when the stronger side performs the prescribed action. The monitoring app 150 may detect this favoring, and either explicitly or internal to the routine, instruct the user to perform the actions to bring both sides into equivalent physical condition. Often this requires the analysis of the long-term performance of a user, and here the storage of data on the local database 178 or on the database of a remote computer (shown in FIG. 13) is useful and is described below. With the monitoring app 150 connected to a network (shown in FIG. 13), the data may be monitored in real-time or afterwards by medical practitioners or others. This has the potential for not just the sharing of information with numerous practitioners, but also the monitoring of the user's progress when not on-site, such as therapy performed in the user's home or other location away from the treatment facility.

In yet another embodiment, the monitoring app 150 may contain a mode wherein the monitoring app 150 instructs the force sensors 30 to turn on for only brief periods of time during a longer duration exercise. This allows data on the user's performance to be sampled throughout the duration of their activity, without the risk of draining the battery 50 as may happen for activities of long duration. Typically the user has entered in the monitoring app 150 an estimate of the duration of their activity, usually measured in hours or fractions thereof. The monitoring app 150 may then pick several times to transition the sensor insoles 10 from a "sleep mode" to a "sprint mode". During the "sleep mode" the force sensors 30 are not acquiring data and the battery 50 is putting out minimal power, only enough to maintain telemetry with the monitoring app 150. At the prescribed times, (the "sprint mode") the monitoring app 150 will instruct the battery 50 to begin a power up cycle, for warming the battery 50 and bringing it to full power. Then the force sensors 30 will be powered and take data for a short span of time, typically about 10 seconds, though the time may be set to be longer or shorter as needed. At the end of the "sprint mode", data collection ceases and the battery 50 is powered down into "sleep mode" as discussed above. "Sprint mode" may be initiated by voice command, touching the touch-sensitive device display 160 of the portable electronic device 140, or pre-programmed.

In yet another embodiment, the monitoring app 150 may contain a mode useful for acquiring data for a sprinter. In this embodiment, the monitoring app 150 signals the user to begin running. In the case of sprinting, there is a time lag between the start of running and the attainment of the rhythmic full speed run. This occurs when the user is accelerating, getting their stride, etc. To save on memory space, data for some predetermined interval, for example two seconds, is not taken. After the two second delay, data is taken normally and throughout the end of the run. Optionally, data may be taken the entire time in order to capture the start as well, as feedback during that phase may be important to the user's performance. Also, if the user is primarily concerned with monitoring starts, the monitoring app 150 may only run for the first few seconds to record just that portion of the run.

The applications of the present invention go far beyond physical therapy. For instance the sensor insoles 10 may be used in the training of an athlete such as a martial artist, runner, or bicyclist, which is discussed in far greater detail in the descriptions of FIGS. 10-12. Here, the training is very similar to physical therapy, where technique can be monitored with feedback provided to the user and/or trainers. Also a history of the user's progress may be formed for use in charting progress and suggestions for further development.

FIG. 7 is a perspective view of the portable electronic device having the monitoring app 150 installed thereupon for monitoring the angular sweep of the user's legs when performing knee extensions. The angle AR, for one leg, labelled "R" on the device display 160 in FIG. 7 for showing that it is the right leg, is defined by a first fixed side 151 (vertical in this embodiment), a first movable side 152 (which remains aligned with the leg in this embodiment), and a first vertex 153 connecting the two. Similarly, the angle AL, for the other leg, labeled "L" in FIG. 7, is defined as having a second fixed side 154, a second movable side 155, and a second vertex 156. Here the two vertexes 153, 156 are located at the same position in the 2-D representation of a user sitting. In this embodiment, the sensor insole 10 may be used as a diagnostic to determine the user's range of motion. For example, the monitoring app 150 may instruct the user to begin in a certain position, such as sitting with the lower leg vertical, by displaying visual cues on the device display 160 or auditory cues through the speaker 162. Specifically, the accelerometer 43 and the gyroscope 44 may determine the change in angle of the foot as the lower leg is lifted at the knee. The accelerometer 43 measures the acceleration in three dimensions, though in this case only the horizontal (in the direction the foot swings out when the leg bends at the knee) and vertical components of the acceleration are relevant to the exercise. The measured values may be sent via the wires 60 to the PCB 40 and ultimately the processor 42 and the memory 46. The processor 42 may further process the data, or it may send it to the transceiver 48 for transmission to the portable electronic device 140. Additionally, the data may be sent to other computers or electronic devices capable of receiving the transmitted data. The monitoring app 150 of the portable electronic device may receive the data and process it further, with the monitoring app 150 converting the measured acceleration data into a change in angle, which may be used independently or compared with the data from the gyroscope 44, which provides a more direct measure of the orientation of the foot. The monitoring app 150 may then show an image of a representation of the user's leg on the device display 160 and/or provide audio information via the speakers 162. As shown in FIG. 7, the swept angles, defined above, for each leg may be superimposed over the image of the user's leg on the device display 160, as well as information which may include, maximum angle, average angle, repetition rate, angular speed, etc.

FIG. 8 is a perspective view of the portable electronic device 140 having the monitoring app 150 installed thereupon for monitoring the forces measured by the force sensors 30 in the sensor insoles 10 and illustrating the data in the form of a pie graph. In FIG. 8, the force data may be shown as a pie graph for each of the force sensors 30, containing the percentage of the user's total weight (or applied force) when standing. Alternatively, with a calibrated system, the absolute values may be displayed. The method of display of the data from the sensor insoles 10 may be displayed as shown or in any other method known to those skilled in the art, and a few of those alternate methods are discussed below as alternative embodiments.

FIG. 9 is a perspective view of the portable electronic device 140 having the monitoring app installed thereupon for monitoring the forces measured by the force sensors 30 in the sensor insoles 10 and illustrating the data in the form of a contour plot. FIG. 9 shows an alternate embodiment of the output of the monitoring app 150 as shown on the device display 160 of the portable electronic device 140. As shown in the FIGS. 8-9 the measurements from the force sensors 30 are processed similarly to the data from the accelerometer 42 and the gyroscope 43 as discussed in the description of FIG. 7. Here, the device display 160 shows a contour map of the intensity of the applied force, at the position of the force sensors 30 on the user's foot. In another embodiment, the displayed image may be a heat or intensity map, with the colors corresponding to surfaces of constant force. Additionally the monitoring app 150 may contain an interpolation program, using methods known to those skilled in the art, to provide a more detailed mapping of the force on the bottom of the foot, which may be helpful for medical applications, in particular. Additional numbers of the force sensors 30 may be placed in the sensor insole 10 to increase the accuracy of the interpolation.

FIG. 10 is a perspective view of the portable electronic device 140 having the monitoring app 150 installed thereupon for monitoring an angle A1 of a user's foot while pedaling a bicycle. Also shown on the device display 160 of the portable electronic device 140 is, a sprocket 14, a crankarm 15, and a pedal 16. The display may be similar to shown in the discussion of FIG. 7, where the angle A1 displayed is formed from a pedal horizontal side P1, a pedal movable side P2, with the two sides meeting at a pedal vertex P3, which in this case is the center of the pedal 16. The pedal horizontal side P1 is taken to be a line through the center of the pedal 16 and parallel to the ground.

FIG. 11 is a perspective view of the portable electronic device 140 having the monitoring app 150 installed thereupon, similar to FIG. 10, wherein the position of the pedal 16 is different than that shown in FIG. 10. The monitoring app 150 is thus able to track the angle A1 throughout the entire movement of the pedal 16, and determine if the user is pedaling efficiently. The angles A1 measured may be compared to optimum angles determined, and recommend better pedaling technique if a user is pedaling in an inefficient manner. In this figure, we also introduce another angle A2, this angle being the angle between a sprocket horizontal side S1, a sprocket movable side S2, and a sprocket vertex S3 where the sprocket horizontal side S1 and the sprocket movable side S2 meet. The sprocket horizontal side S1 is taken to be a line that passes through the center of the sprocket 14 and is parallel to the ground. As in FIG. 10, angle A1 may be labeled with "R" or "L" to indicate which side of the user is being shown by the monitoring app 150.

As the user pedals the bicycle, the image shown on the device display 160 may be updated continuously to show the position of the user's foot and the angle of the foot when on the pedal 16. Also, angle of the other foot may be added as well for comparison, and to help the user attain or maintain bilateral equivalence in their activity, should that be desired.

FIG. 12 illustrates the geometry of a pedal-crankarm system 196 in relation to a force applied by the bicyclist. As illustrated in FIG. 12, the sensor insole 10 (discussed above and illustrated in previous figures) is used to generate data which can then be used to calculate the power generated by the user while biking. The sensor system 300 shown in FIG. 13, and discussed below, may be used to determine the power, and to display the power calculated. The discussion that follows serves to illustrate how various quantities of interest, such as power, may be calculated, and the role of the data from the force sensors 30, the accelerometer 43, and the gyroscope 44 interrelate in doing such. In the following discussion, we state that it is the monitoring app 150 which is performing the analysis, but it may also be performed by another computer system and is not intended to imply that only the monitoring app 150 is capable of, or would be used exclusively for, data analysis.

We must begin with some definitions needed to describe the geometry of the pedal-crankarm system 196. The angle A1 and the angle A2 may be provided by the gyroscopes 44 and the accelerometers 43, respectively, using techniques described below. One embodiment may have the monitoring app 150 numerically integrate the acceleration data stored in the computer memory 176, to obtain angular velocity and position data, and from this determine the angle of the crankarm 15. However, that method may require an initialization routine wherein the user initializes the measurements from rest and at a particular position of the crankarm 15. One way to work around having to perform this initialization may be to use the position data and find minima or maxima. For instance, the maximum vertical position can be taken to be the top of the pedal stroke. That point in time may then be used to set the angle of the crankarm 15. Users skilled in the art may also determine other ways in which to determine the angle of the crankarm 15, the methods considered equivalent and within the scope of the present invention.

Before discussing how the monitoring app 150 may calculate the desired quantities from measurements taken by the force sensors 30, the accelerometers 43, and the gyroscopes 44, it is best to define a few more angles and some vectors used in the analysis. We define a unit vector P, which is a unit vector normal to the pedal 16 and points radially away from the center of the sprocket 14 when the pedal 16 is at its lowest position and horizontal. We also define a vector S, which is a unit vector in the direction from the center of the sprocket 14 radially outward and aligned with the crankarm 15. We also introduce an angle, A3, which is the angle between S and P, and an angle A4, and can be written as, $$A4 = A2 - \pi. \tag{1}$$

Also, A3 may also be written as, $$A3 = \frac{\pi}{2} - A4 - A1. \tag{2}$$

A critical point that needs to be emphasized is that the force sensors 30, in the present embodiment, only measure the force in their direction of actuation, which in this case is normal to the face of the pedal 16. Therefore, the total force on the pedal 16 can be written as $$F1 = \Sigma_i F_i P \tag{3}$$

where $F_i$ is the individual force measurement of a single force sensor 30 and the sum is taken over all force sensors 30. Since we are interested in quantities such as torque and power, it should be realized that these are measured as a result of displacements perpendicular to the direction of the crankarm 15, i.e., motion in a circle. Therefore, it is helpful to consider the magnitudes of the force parallel to the crankarm 15, F2, and perpendicular to the crankarm 15, F3, given by, $$F2 = F1 \cdot S = F1 \cos A3. \tag{4}$$

Then, $$F2 = F1 \cos A3 = F1 \cos\left(\frac{\pi}{2} - A4 - A1\right). \tag{5}$$

Using (1), $$F2 = F1 \cos\left(-\frac{\pi}{2} - A2 - A1\right). \tag{6}$$

With this geometry, F2 is positive when the applied force is pushing away from the center of the sprocket 14, such as at the bottom of a pedal stroke. Likewise F2 is negative at the top of a stroke when the applied force is pushing towards the center of the sprocket 14. The magnitude of the perpendicular component of the applied force is then given by $$F3 = \sqrt{F1^2 - F2^2}. \tag{7}$$

Computing the parallel and perpendicular components of the force may provide the user with detailed feedback on how the force is used during a stroke. For instance, only perpendicular force goes into turning the sprocket 14 and propelling the rider forward. It would be advantageous to minimize the parallel force in order to conserve energy, and the rider could experiment with different techniques to achieve that goal. Such information may be readily displayed to the user on the device display 160, communicated via the speakers 162, or sent to the user output device 170.

The monitoring app 150 may also calculate the amount of energy expended, by the user, in the act of peddling. This has many obvious benefits to the user, such as monitoring improvement, endurance, efficiency, and more. The work done (in the physics context), is the energy expended by pedaling, and can be readily calculated given the above quantities. Work is defined as $$W = \vec{F} \cdot \vec{d}, \tag{8}$$

Where d is the vector describing the motion of the body moving in response to the applied forces. For circular motion, the work done over one revolution may be written as $$W = \int_0^{2\pi} \vec{F} \cdot d\vec{s}, \tag{9}$$

where ds is the differential of arc length due to the rotation of the crankarm 15. In this case, the force is F3 and since F3 is always parallel to ds, the dot product disappears and the integrand may be written as the direct product of F3 and ds.

$$W = \int_0^{2\pi} F3 \, ds = \int_0^{2\pi} F3 R \, d(A2) \tag{10}$$

where R is the length of the crankarm 15, or the radius of the pedal stroke. This equation can easily be numerically integrated by the monitoring app 150 and provide data on the amount of work done (or energy expended). This may also be used to provide a measure of the calories burned due to pedaling, though the conversion between energy expended pedaling and caloric output is not straightforward. Outstanding in this discussion is the determination of R, which may be done in a number of ways. One way is for the user to directly enter in the value. Another way would be for the position data stored in the computer memory 176 to be fit to a circle by the monitoring app 150, with the radius of the circle used as a fitting parameter. A least-squares or other minimization technique known to those skilled in the art, may then be used to quickly, probably within a revolution or two, get a very accurate measure of the radius of the crankarm 15.

The instantaneous power output may be calculated by using the work computations stored in the computer memory 176 over a small time interval, $$\text{Power} = \frac{\Delta W}{\Delta t}, \quad (11)$$

whereas the average power may be computed by using the monitoring app 150 to numerically integrate the instantaneous power over a longer time interval.

Finally, the instantaneous or average torque may be found in a similar manner to the power, using the simple relation, $$\text{Torque} = R(S \times F1) = RF3. \quad (12)$$

All of the above quantities may be stored on the computer memory 176, or other connected computer memories, transmitted to other computers or electronic devices, or displayed individually or in any combination on the device display 160 of the portable electronic device 140. This detailed information is a direct result of the integration of the suite of the force sensors 30, the accelerometers 43, and the gyroscopes 44 with the monitoring app 150 or other computer programs that may serve to analyze and process the data.

In another embodiment, the sensor insoles 10 may be used in another way to aid in the training of a bicyclist, as mentioned above. When a person is peddling a bicycle, they not only push down on the pedal 16 for half of a peddling cycle, but also pull up for the other half of the peddling cycle. This of course applies only when using pedal straps, clipless pedals, or similar accessories where the foot is bound to the pedal 16. When pulling up during the bottom of the cycle, the foot should move from parallel to the ground to an angle of about 45 degrees. The gyroscope 44 in the sensor insoles 10 is able measure the angle of the foot during the cycle. Also, as a foot is pulling, the natural lever between balls of the foot and the heel puts force on the front force sensors 30. In this way, a direct measure of the force applied during an upward cycle may be measured. Also, sans pedal clips, a user's leg should be just resting when it is on an upstroke, in other words, not pushing down and resisting the motion of the other leg. The force sensors 30 may detect increased force over an established baseline to provide feedback to the user that they may be applying unwanted force and to correct it. Also, the skilled bicyclist will use each leg evenly during a ride. Because the various forces may be measured on both feet, the movements may be analyzed by the monitoring app 150 to determine if bilateral equivalence is present. Feedback may then be given to the user, via the monitoring app 150 or other computerized form of communication, for improving their peddling action.

The sensor system 300 (shown in FIG. 13) may be used for monitoring and reporting power exerted by a person riding a bicycle. The sensor system 300 comprises the sensor insole 10 (such as is shown in FIG. 1), and the portable electronic device 140 (shown in FIG. 6). In this embodiment, the monitoring app 150 (shown in FIG. 6) is in the form of a power measurement program operably installed in the computer memory 176 of the portable electronic device 140.

Figure 13:
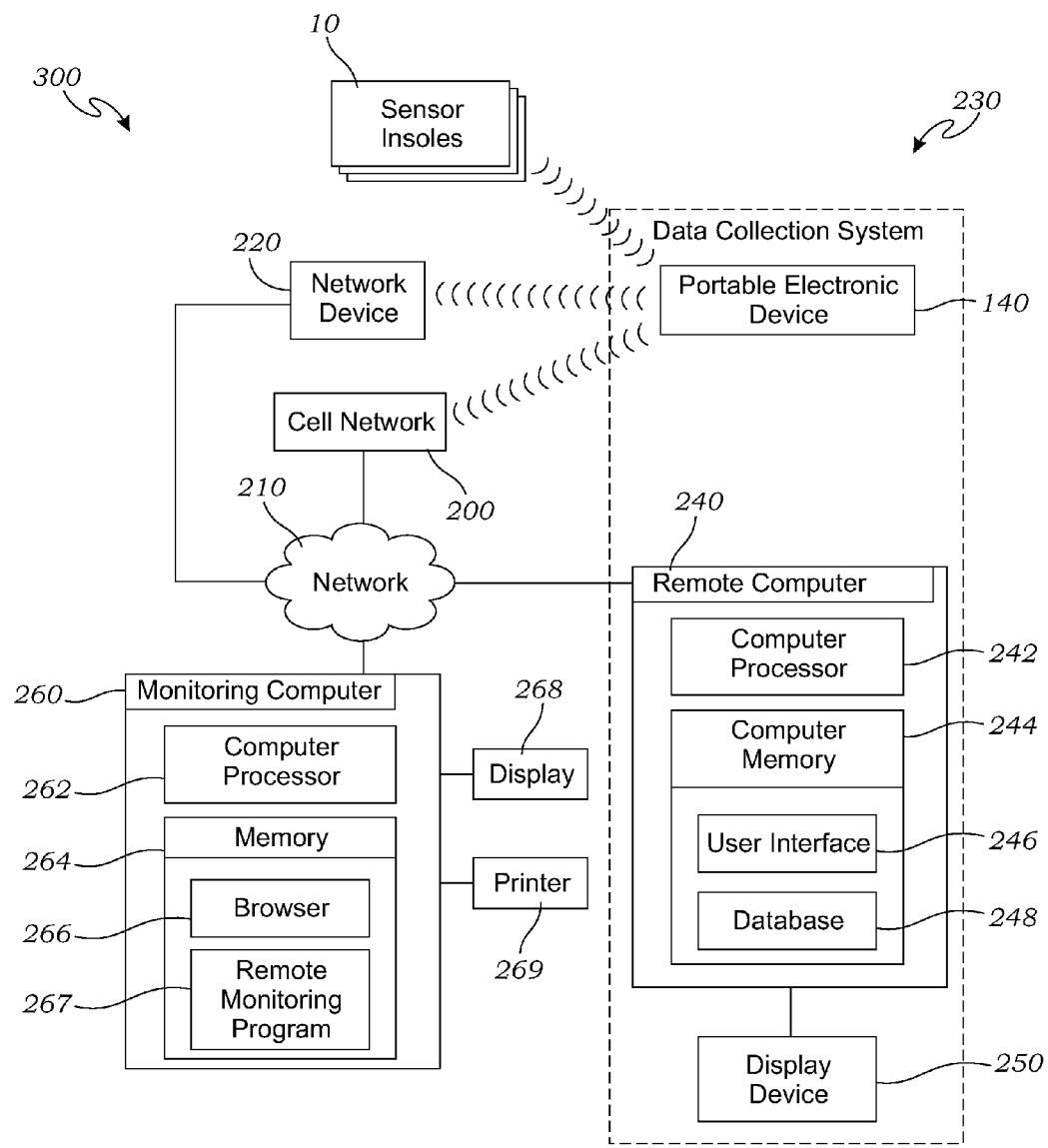
FIG. 13 is a block diagram of one embodiment of a sensor system that includes the portable electronic device, a monitoring computer, and a remote computer for monitoring the sensor system and storing data.

As shown in FIGS. 1, 6, and 13, the power measurement program 150 receives data from the accelerometer 43 regarding movement of the sensor insole 10, and receives data from the force sensors 30 to determine a force exerted by the person again the pedals via the substrate layer of the sensor insole. As noted above, the accelerometer 43 may include one or more accelerometers. The power can then be calculated based upon the data received, and the power may then be outputted to and displayed on the computer display 160 of the portable electronic device 140, as discussed in greater detail below.

In one embodiment, the power measurement program 150 may perform the following steps: determining a cadence based upon the data from the accelerometer; calculating a torque based upon the force measured; and calculating the power based upon the torque and the cadence.

For purposes of this application, the terminology of computing "power" and displaying "power" is hereby defined to include any particular form of power or equivalent measure. This may include an instantaneous measurement, an average over time, peak power, and average peak power, to name a few.

In one embodiment, the power measurement program 150 may measure a peak power for every rotation of the pedals, and report the peak power measured via the computer display of the portable electronic device.

In another embodiment, the power measurement program 150 may measures a peak power for every rotation of the pedals, determine an average peak power by averaging the peak power for a number of rotations of the pedals, and report the average peak power on the computer display of the portable electronic device.

In one embodiment, the power measurement program 150 may measure a total power for every rotation of the pedals, determine an average power by averaging the power measurements for a predetermined number of rotations of the pedals, and report the average power on the computer display of the portable electronic device.

In one embodiment, the power measurement program 150 may determine a waveform using total acceleration on the Y and Z axes of the accelerometers; determine an average time from peak to peak of the waveform and extrapolate that over a period of time to determine a cadence; calculate a power based upon the cadence and the force data received from the force sensors; and output the power calculated on the computer display of the portable electronic device.

The output of the data is described in greater detail below with reference to FIGS. 22 and 23.

FIG. 13 is a block diagram of one embodiment of a sensor system 300 that includes the portable electronic device 140, a monitoring computer 260, and a remote computer 240 for monitoring the sensor insole 10 and storing data. The sensor insoles 10, in the present embodiment, are connected to the portable electronic device 140, as described above, which in the present embodiment the portable electronic device 140 is a cellular telephone, the portable electronic device 140 streams data to/from a cellular network 200. The cellular network 200 may then be connected to another network 210, which may be a local area network ("LAN") or a wireless network. Alternatively, in another embodiment, the portable electronic device 140 may communicate with the network 210 through a network device 220 such as a wireless transceiver or router. Here we consider two computers in the present embodiment of the invention, the remote computer 240 and the monitoring computer 260.

The remote computer 240 has a computer processor 242, a computer memory 244, a user interface 246 operably installed in the computer memory 244, a database 248 operably installed in the computer memory 244, and a remote display 250. The remote computer 240 functions primarily as a repository of data taken during the user's activity. Data stored on the remote computer 240 may be accessed via the network 210 by other computers, or viewed locally using the remote display 250.

The monitoring computer 260 has a computer processor 262, a computer memory 264, a browser 266 operably installed in the computer memory 264, and a monitoring program 267 operably installed in the computer memory 264. Also, the computer may be connected to a monitoring display 268 for viewing the data and/or the output of the monitoring program 267, and have a printer 269 for printing physical copies of the same. The browser 266 may be a typical internet browser or other graphical user interface ("GUI") that may allow communication over the internet to the patient, other health care practitioners, or trainers. The monitoring program 267 interprets the results of the data sent by the monitoring app 150 and provides analysis and reports to the user of the monitoring computer 260. The monitoring program 267 provides information not included in the monitoring app 150, for example diagnosis of conditions and suggestions for treatment, or comparison of results with other patients either in real-time or by accessing the database 248 of the remote computer 240.

One embodiment of the sensor system 300 includes providing the various components, particularly the force sensors 30, a unique address programmed therein for identification. The sensor system 300 includes a data collection system 230 for simultaneously monitoring both the first and second locations and, in addition to any other number of locations that may be desired, around the world.

In this embodiment, the data collection system 230 may include a cell phone (such as is shown in FIG. 5), and the remote computer 240 for simultaneously monitoring both the first location and a second location. In alternative embodiment, any one of these elements, or combinations thereof, may be used, in addition to any additional computer devices for tracking the data.

In this embodiment, a unique address is stored in each of the various components, and may include an IP address, or any form of unique indicator (e.g., alphanumeric). The address may be stored in the memory 264 (illustrated in FIG. 7), or in any other hardware known in the art, and is transmitted with the data so that the data may be associated with the data in a database (e.g., the local database 178 of the portable electronic device 140, or the database 248 of the remote computer 240). This method is discussed in greater detail below.

Data from the various components may then be streamed to the remote computer 240 (or other component of the data collection system 230) for storage in the database 248. For purposes of this application, "streaming data" may be performed in real time, with data being constantly transmitted (e.g., in typical "packets"), or it may be aggregated and sent periodically, or it may be stored and periodically downloaded (e.g., via USB or other connection) and transmitted.

In one embodiment, such as that illustrated in FIG. 10, the data may include force data from the at least one of the force sensors 30, and movement data from the at least one of the accelerometers 43. Selected data, such as the force data, may be transmitted in real time, while more complex data, such as the movement data may be stored in the memory 46 until a suitable trigger, such as actuation of a pushbutton, passage of a predetermined period of time, or other trigger (e.g., at the end of an exercise), and then streamed as a single transmission. Transmitting the data in this manner has proven to greatly relieve demands on the sensor insoles 10, which might otherwise make management of the data extremely difficult, especially when large numbers of users are utilizing the system.

In one embodiment, the data may be periodically analyzed by the remote computer 240 (or other suitable computer system) for "alarm conditions" (e.g., information and/or deviations that may be of interest to the user and/or the doctor and/or any other form of administrator). If an alarm condition is detected, a pertinent alert may be sent to the monitoring computer 260, directly to the user (e.g., via text message, email, signal to the portable electronic device 140, etc.), or to any other suitable party. For example, if the user is putting too much force on an injured leg during rehabilitation, or performing the exercise incorrectly, an alert may be sent to the user for immediate action, and/or a message (e.g., training video, etc.) may be sent via email or other method to help the user perform the exercise correctly.

In another embodiment, in which the sensor system 300 is used in an industrial setting, reports may be sent to supervisors to correct incorrect behavior of workers. In the case of monitoring workers compensation recipients, a fraud monitor may be alerted if the recipient is detected acting in a manner inconsistent with their injury (e.g., playing a sport).

Figure 14:
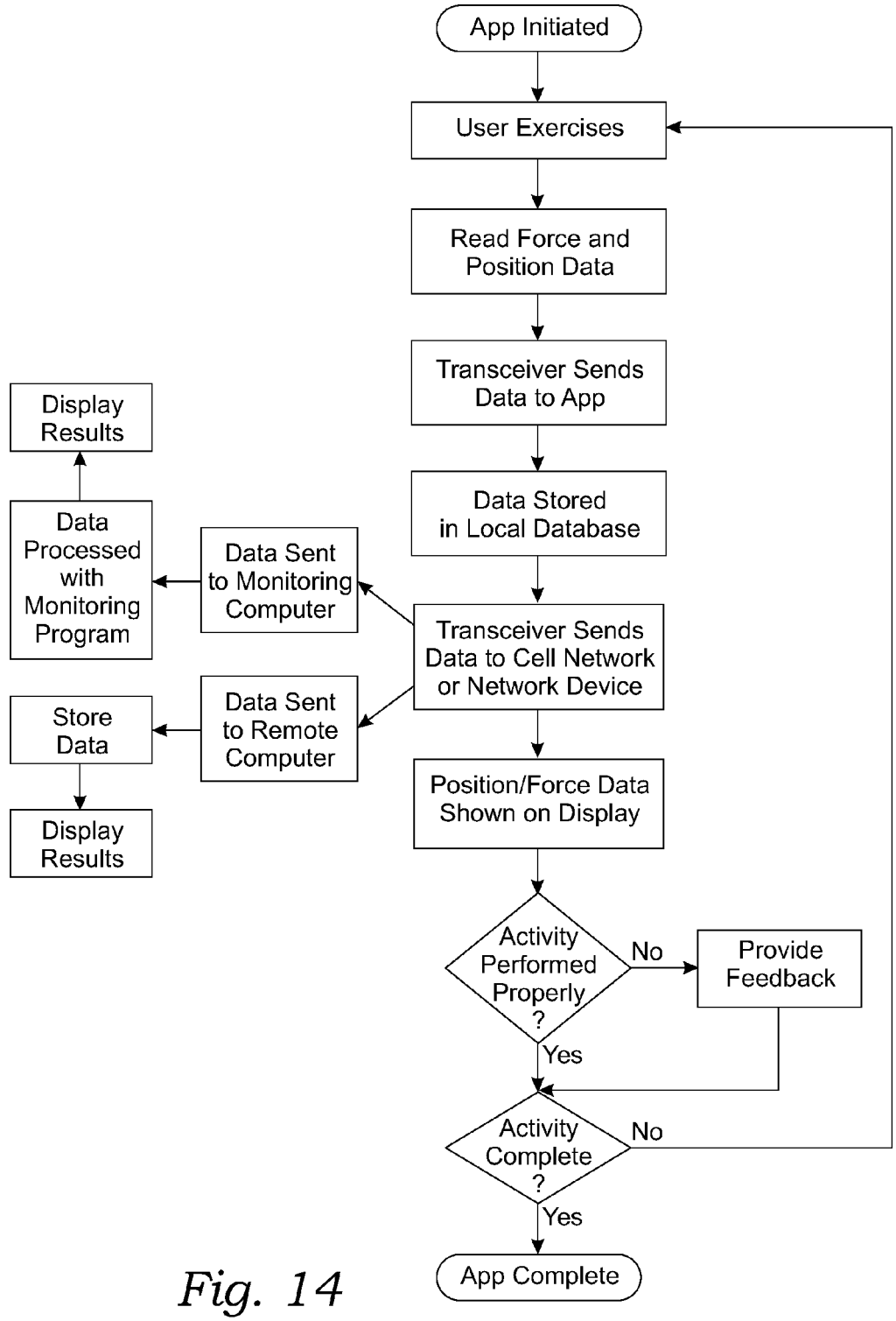
FIG. 14 is a flow diagram illustrating the operation of the sensor system of FIG. 13.

FIG. 14 is a flow diagram illustrating the operation of the sensor system 300 of FIG. 13. The flow diagram is illustrating one possible activity utilizing the sensor system 300, in this case the act of performing an exercise such as might be required for physical therapy. The flow chart is not meant to exclude any functionality of the other embodiments described in the application. Also, the flow chart of FIG. 14 is used only to illustrate one possible flow of the functions of the sensor insoles 10 and other connected systems, and should not be considered as an exclusive flow of function. As shown in FIG. 14, the monitoring app 150 is initiated at which point the user begins to exercise. The force sensors 30 take data and the data is sent via the transceiver 48 to the remote electronic device 140. The monitoring app 150 receives the data and stores a copy in the local database 178 in addition to sending a copy to the cellular telephone network 200 or the network device 220. The cellular network 200 or the network device 220 then communicates with another network 210, typically a LAN as described above, wherein the data may be distributed to the monitoring computer 260 and/or the remote computer 240. The monitoring computer 260 processes the data with the monitoring program 267 and displays the results, on the monitoring display 268, to the user of the monitoring computer 260. The remote computer 240 may store data on the database 248 of the remote computer 240 and may also display results on the remote display 250 device of the remote computer 240. Meanwhile, on the monitoring app 150 position and/or force information may be shown to the user of the monitoring app 150 on the device display 160. The monitoring app 150 then determines if the user is properly performing the activity. If not, then feedback is provided to the user using audio and/or visual cues as described above. The activity continues until completed by the user or the monitoring app 150 determines that it is time to stop, at which time the monitoring app 150 completes its operation.

Figure 15:
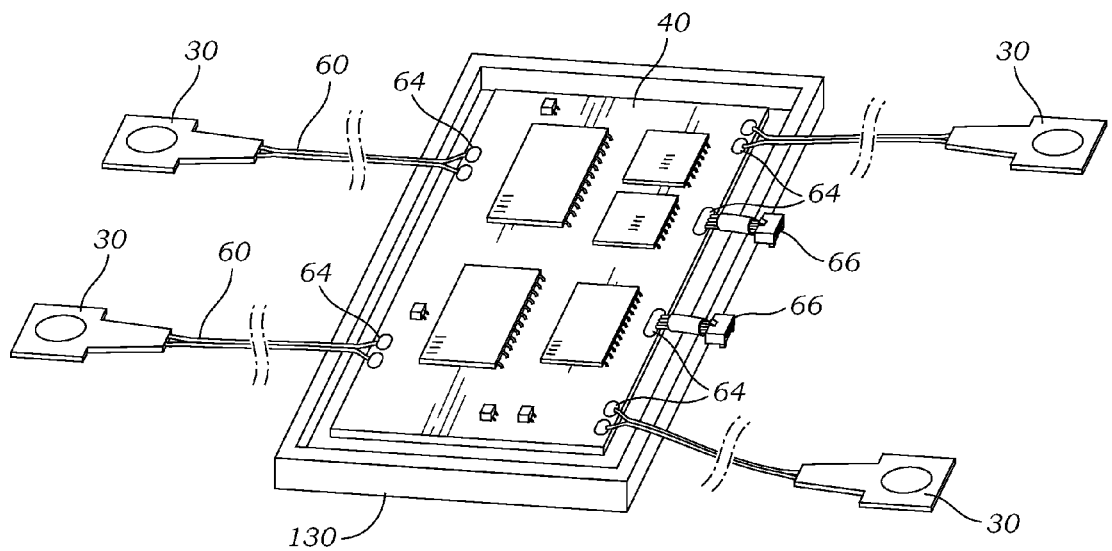
FIG. 15 is a perspective view of the printed circuit board of FIG. 1 placed in a bottom portion of a mold adapted for application of an epoxy layer to the printed circuit board.
Figure 16:
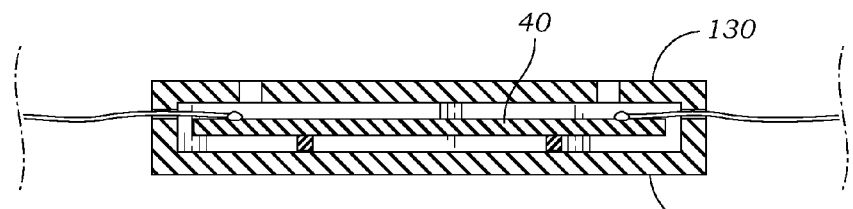
FIG. 16 is a sectional view of the mold closed around the printed circuit board.
Figure 17:
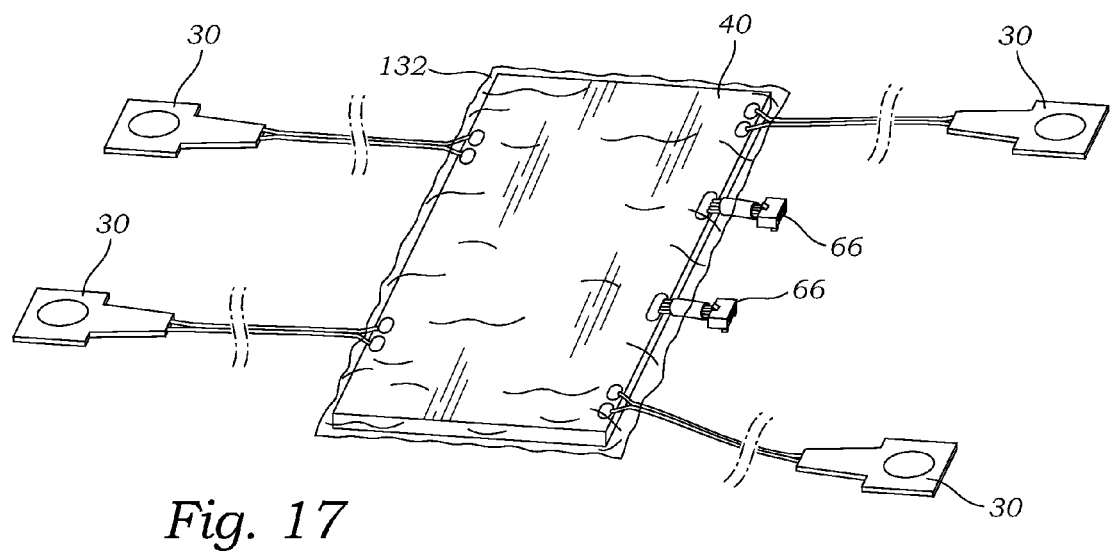
FIG. 17 is a perspective view of the printed circuit board encased in the epoxy layer formed in the mold of FIGS. 15 and 16.

FIG. 15 is a perspective view of the printed circuit board 40 of FIG. 1 placed in a bottom portion of a mold 130 adapted for application of a protective layer 132 (e.g., epoxy or other suitable material) to the printed circuit board 40. FIG. 16 is a sectional view of the mold 130 closed around the printed circuit board 40. FIG. 17 is a perspective view of the printed circuit board 40 encased in the epoxy layer 132 formed in the mold of FIGS. 15 and 16.

As illustrated in FIGS. 15-17, the mold 130 is used to encase the printed circuit board 40 in the epoxy layer 132. The method of encasing the printed circuit board 40 in the epoxy layer 132 may utilize an epoxy mold 130, as illustrated, or similar/equivalent protective materials may be applied in any other manner known to those skilled in the art. The printed circuit board 40 may be positioned in the epoxy mold 130 so that it substantially surrounds the printed circuit board 40, or at least a weak portion of the printed circuit board 40. Next, an epoxy or similar/equivalent material is injected into the epoxy mold 130 to substantially surround the printed circuit board 40 with the epoxy layer 132, such that the epoxy layer 132 also surrounds the solder joints (e.g., of the wires 60) of the printed circuit board 40.

The printed circuit board 40 is then removed from the epoxy mold 130, and the epoxy layer 132 is allowed to cure. The specific methods used to form the epoxy layer 132 may be varied by one skilled in the art, and similar and/or equivalent methods should be considered within the scope of the present invention. In one embodiment, for example, only the solder points are covered with the epoxy layer 132. In another embodiment, only select components on the printed circuit board 40 may be covered with the epoxy layer 132. Other methods of protecting the solder joints may be used, such as melting a plastic or other material around them, heat shrinking wraps, crimping protective lugs, etc. Variations of the method known to one skilled in the art may also be used and the above steps are not to be considered as exclusive of any equivalent methods.

When the printed circuit board 40 is ready, whether coated with epoxy or not, it is assembled with the other components of the sensor assembly 20. The assembly can be performed using any methods known to one skilled in the art. Some components, such as the force sensors 30, may be attached directly with wires (e.g., the wires 60) that are soldered to the printed circuit board 40. Other components may be attached at a later time via connectors 66. In the preferred embodiment, the sensor assembly 20 is assembled using a jig to correctly position the various components to predetermined positions relative to each other.

Figure 18:
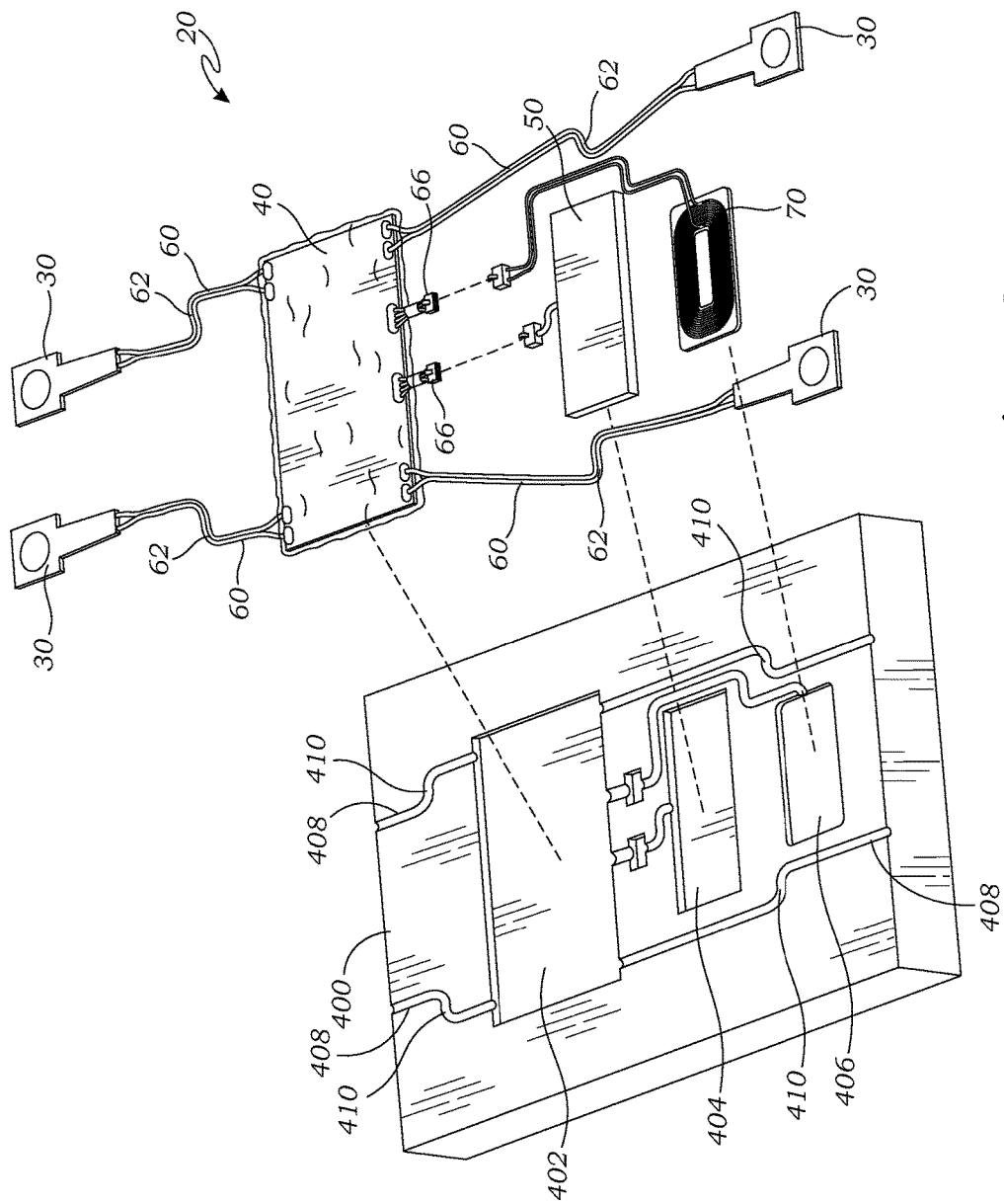
FIG. 18 is a perspective view of the sensor assembly being assembled in a sensor jig.

FIG. 18 is a perspective view of the sensor assembly 20 being assembled in a sensor jig 400. The sensor jig 400 is useful in the current method for manufacturing the sensor insole 10, as it enables the precise assembly of the various components described above, so that the components are positioned correctly for gathering the necessary data, without breaking. In one embodiment, the plurality of the force sensors 30 are attached to the PCB 40 via the wires 60, as discussed above. The solder connection between the wires 60 of each of the force sensors 30 and the printed circuit board 40 may be covered with the epoxy layer 132.

The sensor jig 400 may include guide features 402 such as a PCB receiving space (i.e., recess) shaped to receive the printed circuit board 40. The sensor jig 400 may also include a battery receiving space 404 shaped to receive the battery 50, an inductive charging coil receiving space 406 shaped to receive the coil 70, and wire grooves 408 for receiving the wires 60. The sensor jig 400 positions the various components in a predetermined configuration that is optimal for the function of the sensor assembly 20, and correctly positions the force sensors 30 for sensing force from the foot of the user at the correct predetermined locations on the foot. Each of the sensor jigs 400 may be designed to prepare a sensor device 10 that is specific for a particular shoe size (or range of sizes). The predetermined configuration may include having the wire grooves 408 possessing S-bends 410, for correctly positioning the wires 60 in the S-shape described above, between the printed circuit board 40 and the force sensors 30.

Once the sensor assembly 20 is assembled on the sensor jig 400, it is ready to be positioned on the felt layer 90 (as shown in FIG. 2).

In another embodiment, the sensor jig 400 may be formed by a very thin layer (e.g., plastic), and may further include an adhesive (not shown) on the top surface, so that the various components described above may be easily mounted on the sensor jig 400 and held in place by the adhesive (and potentially depressions similar to the construction described above). In this embodiment, the sensor jig 400 may be physically positioned on the felt layer along with the components, and due to the thin construction, the sensor jig 400 may be molded into the insert.

Figure 19:
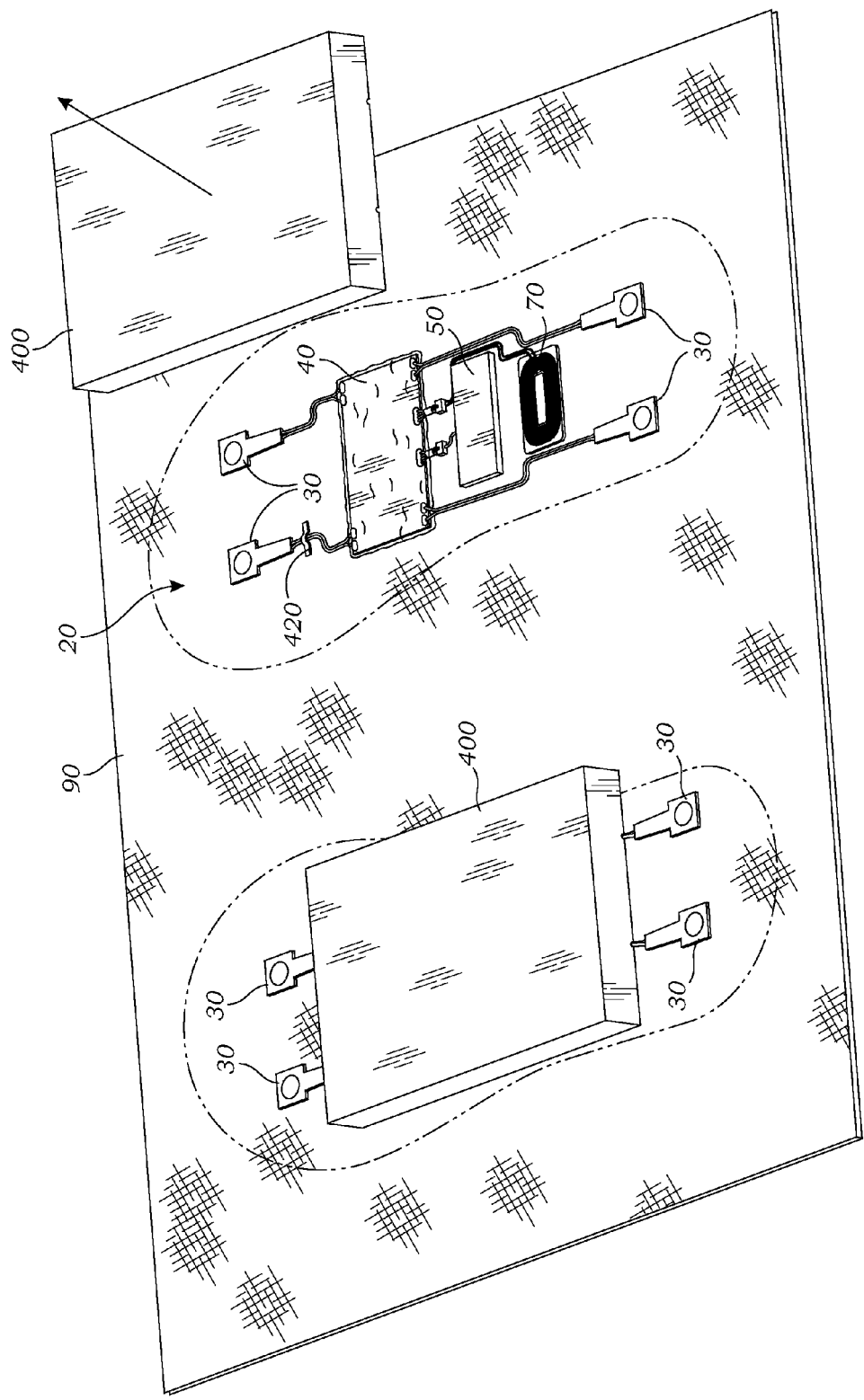
FIG. 19 is a perspective view of the sensor assembly, in the sensor jig, being positioned on the felt layer.

FIG. 19 is a perspective view of the sensor assembly 20, in the sensor jig 400, being positioned on the felt layer 90. As shown in FIG. 19, the sensor jig 400 enables the transfer of the sensor assembly 20 to the felt layer 90 without loss of the predetermined configuration. To retain the position of the sensor assembly 20 on the felt layer 90 after removal of the sensor jig 400, a fastening element 420 may be used to fasten the sensor assembly 20 to the felt layer 90. In one embodiment, the fastening element 420 may be an adhesive tape. In other embodiments, it may be any form of clip, pin staple, layer of adhesive (not shown), and/or any other feature for attaching the sensor assembly 20 on the felt layer 90.

After positioning the sensor assembly 20 on the felt layer 90, the felt layer 90 may be forwarded for application of the urethane layer 120, as discussed above with reference to FIGS. 2-4.

Figure 20:
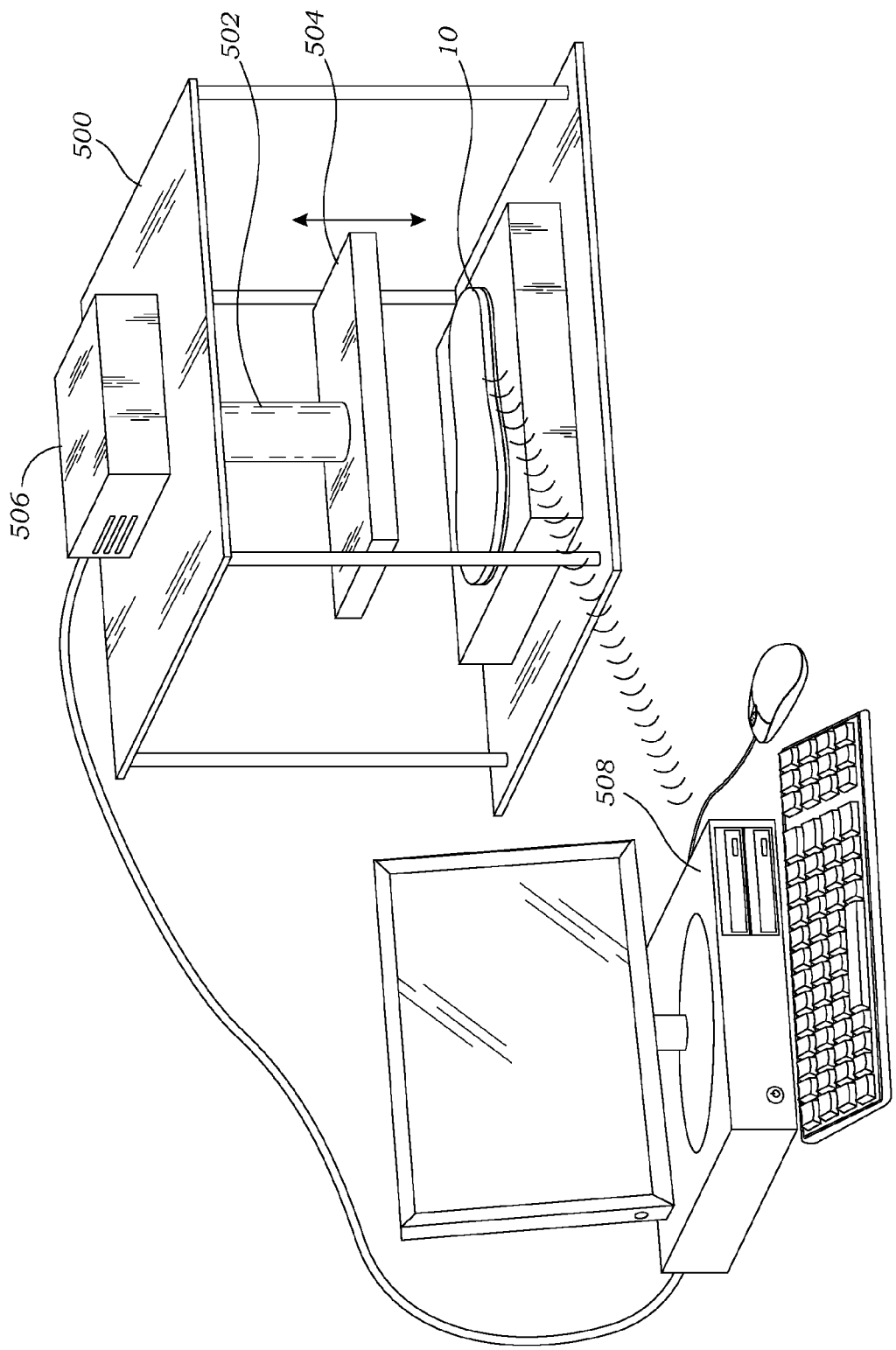
FIG. 20 is a perspective view of one embodiment of a calibration device providing force to the sensor insole.

FIG. 20 is a perspective view of one embodiment of a calibration device 500 providing force to the sensor insole 10. FIG. 20 illustrates one step of a process known as "characterizing and conditioning" of the sensor insole 10. The "characterizing" part of it refers mainly to a calibration of the force sensors 30 in the sensor insole 10. The force sensors 30 in the sensor insole 10 provide an electrical measurement of the amount of applied force. The output of the force sensors 30 may be read as a voltage, a resistance, or a current, proportional to the applied force. Because each force sensor 30 in the sensor insole 10 may be different, as well as the varying distribution of the surrounding urethane layer 120, the output of the force sensors 30 needs to be calibrated to enable the monitoring app 150 to properly interpret the data. Although the force sensors 30 may be calibrated when not in contained in the urethane layer 120, it is preferable that an in-situ calibration of the sensor insole 10 is performed, in order to have a calibration that will be more accurate under normal use.

The present application includes a method of calibration having the steps of first providing the calibration device 500 and the sensor insole 10 having force sensors 30 (FIG. 1). In one embodiment, the calibration device 500 may have an actuator 502 connecting a pressure plate 504 to a motor 506. The control of the calibration device may be done by interfacing with a calibration computer 508. The sensor insole 10 may be placed in the calibration device 500. Then the calibration computer may instruct the motor 506 to drive the actuator 506 to move the pressure plate 504, applying force to the sensor insole 10. The sensor insole 10 may then transmit the data from the force sensors 30 back to the calibration computer 508. The calibration computer 508 may then determine the calibration conversion needed to translate the signals from the force sensors 30 into an applied force measurement. This step may be repeated with numerous values of known forces applied by the calibration device 500. Finally, the calibration data may be saved by the calibration computer 508 or stored in the memory 46 (FIG. 1) of the sensor insole 10.

The "conditioning" part of the process may be used to prepare the sensor insole 10 for use, or for an additional calibration. The procedure of applying force repeatedly to the sensor insole 10 may lead to a permanent or semi-permanent compression of the urethane layer 120. As this may have an effect on the calibration of the force sensors 30, this step is preferably done prior to a final calibration.

Variations of the method may include, but not be limited to, allowing a resting time before taking the calibration measurement, as the force sensors 30 are surrounded by an elastic material that may need time to settle. Repeating the calibration for differing designs or thicknesses of the urethane layer 120 may also be done. Individual prongs (not shown) may be used with the pressure plate 504 to apply force concentrated only at the location of the force sensors 30, to reduce the distortion from any of the structure of the urethane layer 120 on the calibration.

Those skilled in the art may devise other methods of calibrating the sensor insole 10, or using additional techniques, such variations being considered equivalent and within the scope of the present invention.

Another process which may be included in the method is to provide a production database, where each sensor insole 10 may be associated with a unique identification code. The codes may then be stored in the production database and associating the unique identification codes with the calibration information corresponding to the appropriate sensor insoles 10. Two sensor insoles 10 may then be paired. At this point, two checks may be done. First, confirming that calibration information has been received for each of the force sensors 30 of each of the two sensor insoles 10 that are being paired. Second confirming the pairing if all of the calibration information is in the production database, or, if not all of the calibration information is in the production database, refusing the pairing. Additional steps in this production method may be included or omitted as determined by one skilled in the art. Also the details of what constitutes an acceptable pairing may also be varied.

Figure 21:
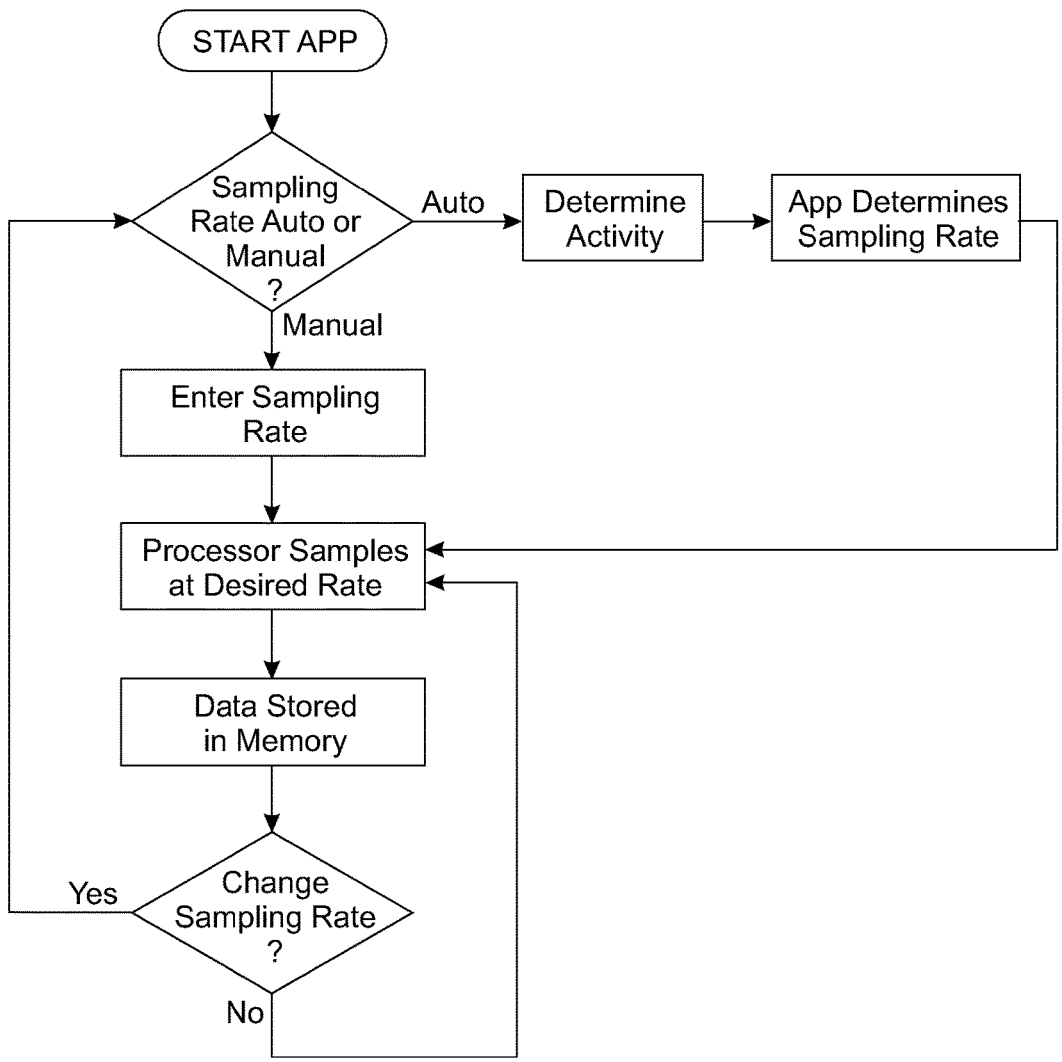
FIG. 21 is a flow diagram illustrating the steps in determining the sampling rate of the sensor insole.

FIG. 21 is a flow diagram illustrating the steps in determining the sampling rate of the sensor insole 10. As previously discussed, measurements of the force applied to the force sensors 30 are taken to provide information about the activity of the user of the sensor insole 10. The sampling rate is the rate, typically given in samples per second, or Hertz (Hz), that force measurements from the force sensors 30 are read by the processor 42 of the PCB 40. The sampling rate may be determined by a user's activity, or entered manually.

The present invention includes a method for varying the sampling rate of force sensors of a sensor insole 10, the method comprising the steps of first providing the sensor insole 10 having the processor 42 and the memory 46. Also, providing the monitoring app 150 to control the operation and interface with the processor 42. Once the components are provided, starting the monitoring app 150 which will interface with the processor 42 of the sensor insole 10. Next, selecting if the sampling rate is determined automatically or manually. If the sampling rate is to be determined automatically, determining the present activity of the user and determining the sampling rate, both via the monitoring app 150. If the sampling rate is to be determined manually, determining the sampling rate via input from a user. When data is being taken, data is sampled from the force sensors 30 at the selected sampling rate to create sampled data. The sampled data may then be stored in the memory 46 of the processor 42. The monitoring app 150 or the processor 42 may be programmed to querying for a change in sampling rate. If such queries are made, the sampling rate may be changed according the results of the query. The acquisition of data may be stopped at any time by the user or by the monitoring app 150.

Preferably, the sampling rate is the minimum required sampling rate to provide the resolution needed by the user of the sensor insole 10. Undersampling may result in insufficient data or errors resulting from any interpolation or graphical representation of the sparse data set. Oversampling may result in limiting the time period of data that may be stored in the memory 46, or creating unnecessarily large and cumbersome data files. Other methods of post-processing the sampled data may include binning routines to average sampled data according to specified time windows. Also spline fitting or polynomial fitting routines may be used generate an accurate representation with a continuous mathematical function rather than a large set of discrete data points. Further processing of the data may be done according to methods known to one skilled in the art.

Figures 22, 23:
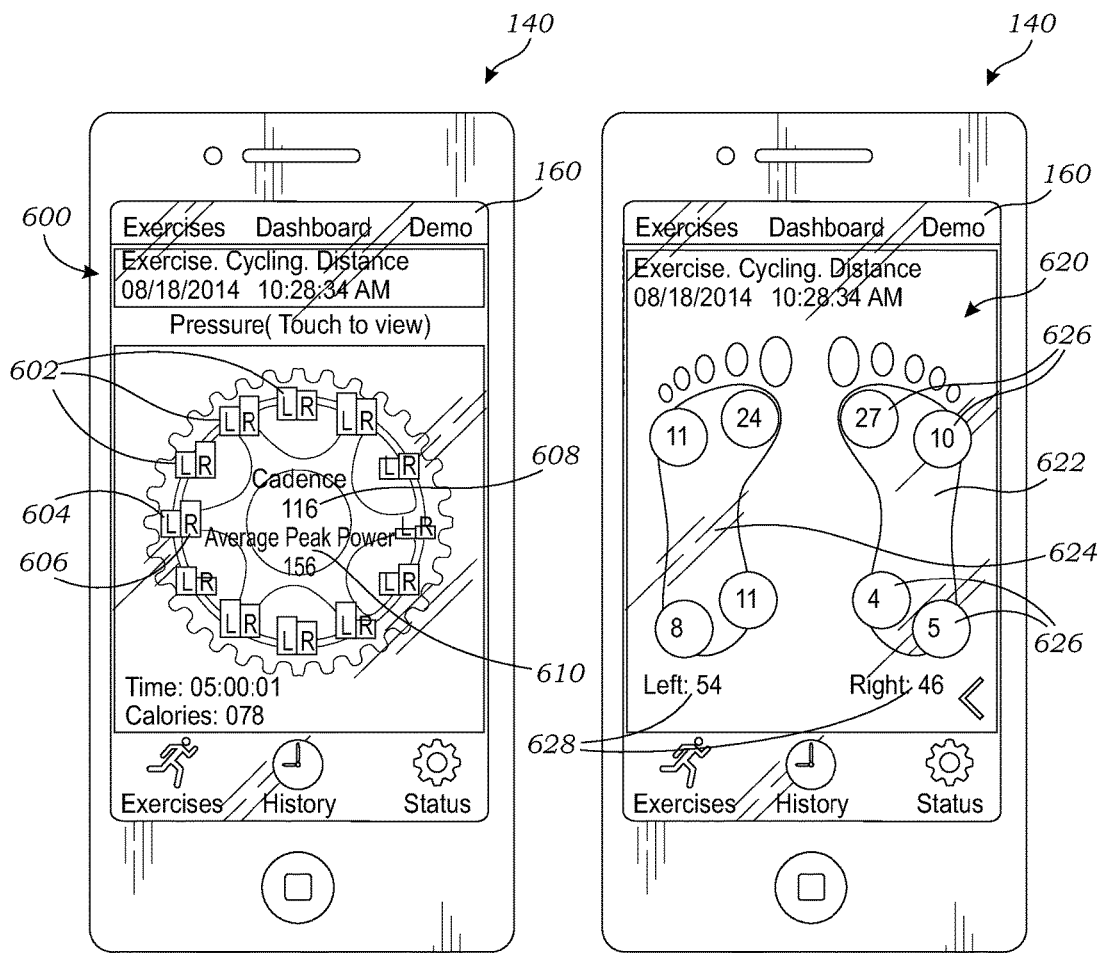
FIG. 22 is a perspective view of the portable electronic device illustrating a cycling power output according to one embodiment of the present invention.
FIG. 23 is a perspective view of the portable electronic device illustrating a force output that illustrates the force generated by the feet of the user during one portion of the cycling power output of FIG. 22.

FIG. 22 is a perspective view of the portable electronic device 140 illustrating a cycling power output according to one embodiment of the present invention. As discussed above with reference to FIGS. 10-12, the power may be determined using many methods, some of which are described above. The power calculated is then outputted for computer display 160 on the portable electronic device 140 (and/or other computer devices, either locally or remotely via network).

In the embodiment of FIG. 22, the power is displayed in many ways, to provide the cyclist with as much actionable feedback as possible. In this embodiment, the computer display 160 includes a pedal-crankarm display 600 that includes multiple power points 602 displayed in different angular positions around the pedal-crankarm. Each of the power points 602 includes a left power indicator 604 and a right power indicator 606 that each indicate the power measured at this point, by the left and right insoles, respectively. A bar graph may be used, as shown, or other forms of indication (e.g., colors, numbers, other forms of graphs, etc.).

In this embodiment, the pedal-crankarm display 600 may further include a cadence indicator 608 to indicate the cadence that is being maintained (in RPM, or other suitable method), and an average peak power 610. In this embodiment, these displays are numeric; however, other display options may also be used, as mentioned above. These and other options are discussed in greater detail, along with examples of how they are computer, above, with reference to FIGS. 10-12.

In one embodiment, the user is able to pre-set his or her cadence, either for a given ride, or even for different parts of the ride (e.g., warm up, middle, and cool down portion of the ride). The system then compares the selected cadence against the actual cadence, and can provide feedback (e.g., if the rider is too fast, too slow, or maintaining proper cadence). The feedback may be audible (e.g., beeping, verbal guidance, etc.), visual (e.g., flashing lights, graphic), vibrational, and/or any combination of these methods of other methods known in the art.

In a similar manner, these techniques may also be applied to running A user is able to predetermine his or her cadence or gait. The system is able to measure running power (specifically, acceleration) and other characteristics of the runner, for determining if the runner is performing as desired. The runner may predetermine particular cadences for various parts of a run, and the system will report whether the runner is meeting his or her predetermined goals. The system is also able to report other characteristics of the runner, such as whether he or she is running correctly and in good form, and also maintaining proper bilateral equivalence. This data can be reported back while the run is in process, and/or reported after the run, so that techniques may be improved and additional training added to correct deficiencies.

FIG. 23 is a perspective view of the portable electronic device 140 illustrating a force output 620 that illustrates the force generated by the feet of the user during one portion of the cycling power output of FIG. 22. In this embodiment, FIG. 23 is generated when a user selects one of the power points 602, and FIG. 23 provides more detailed information about this power point 602.

In the current embodiment, the force output 620 includes a graphic image of a right foot 622 and a left foot 624, and each graphic image includes a plurality of force points 626 that may correspond to individual force sensors 30 discussed above (with reference to FIG. 1). These force points 626 show how a total power 628 of each foot is spread over the foot, indicating whether the user is pushing the pedals efficiently, or ineffectively.

All of the data output can then be analyzed by the cyclist (or trainer, doctor, etc.) to determine if the cyclist is using proper form, and exerting correct power. If the foot is incorrectly positioned or pushed, or if the cyclist is exerting himself either too much or too little, corrective action can be taken so that the cyclist exerts himself or herself with peak efficiency.

This system can also check for bilateral equivalence, to make sure that the cyclist is equally using his or her left and right feet, and not favoring one over the other. If the power is being generated in an unbalanced manner (due to bad habits, an injury, or other reason), corrective action can be taken to return the user to correct bilateral equivalence.

The computer or computers used in the sensor system may be any form of computers or computers, servers, or networks known in the art. As used in this application, the terms computer, processor, memory, and other computer related components, are hereby expressly defined to include any arrangement of computer(s), processor(s), memory device or devices, and/or computer components, either as a single unit or operably connected and/or networked across multiple computers (or distributed computer components), to perform the functions described herein.

The exemplary embodiments described herein detail for illustrative purposes are subject to many variations of structure and design. It should be emphasized, however that the present invention is not limited to particular method of manufacturing sensor insoles as shown and described. Rather, the principles of the present invention can be used with a variety of methods of manufacturing sensor insoles. It is understood that various omissions, substitutions of equivalents are contemplated as circumstances may suggest or render expedient, but the present invention is intended to cover the application or implementation without departing from the spirit or scope of the claims.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. The term 'shoes' or 'footwear' may have been used above interchangeably and refer to convey the same meaning. The term "activity" as used in this application refers to any activity that the user of the present invention may be undertaking, whether it is exercise, training, physical therapy, or routine activities. Also, pressure and force may be used interchangeably as pressure is simply a scalar quantity that relates the applied force to a known surface area. Furthermore, the terminology used in the specification provided above is hereby defined to include similar and/or equivalent terms, and/or alternative embodiments that would be considered obvious to one skilled in the art given the teachings of the present patent application.

What is claimed is:

1. A method for monitoring power exerted by a person riding a bicycle with pedals, the method comprising the steps of:
   providing a pair of sensor insoles, each of the sensor insoles having a substrate layer having a plurality of force sensors, an accelerometer, a transmitter for transmitting data from the plurality of force sensors and the accelerometer, and a battery operably connected to a printed circuit board having a computer processor and a computer memory;
   providing a portable electronic device having a computer processor and a computer memory for receiving the data transmitted from the transmitters of the sensor insoles, and further including a computer display;
   positioning the pair of sensor insoles within shoes being worn by the person so that the sensor insoles are positioned beneath the feet of the person;
   receiving the data transmitted from the pair of sensor insoles to the portable electronic device while the person rides the bicycle;
   determining a waveform using total acceleration on the Y and Z axes of the accelerometers;
   determine an average time from peak to peak of the waveform and extrapolate that over a period of time to determine a cadence;
   calculating power based upon the cadence and the force data received from the force sensors;
   outputting the power calculated on the computer display of the portable electronic device;
   receiving a predefined cadence from the person;
   comparing the cadence calculated to the predefined cadence; and
   reporting if the cadence is the same as or different from the predefined cadence.

2. The method of claim 1, further comprising the following steps:
   calculating a torque based upon the force measured by the force sensors; and
   computing the power using the torque and the cadence.

3. The method of claim 1, further comprising the following steps:

measuring a peak power for every rotation of the pedals; and reporting the peak power measured via the computer display of the portable electronic device.

4. The method of claim 1, further comprising the following steps:

measuring a peak power for every rotation of the pedals;

determining an average peak power by averaging the peak power for a number of rotations of the pedals; and reporting the average peak power on the computer display of the portable electronic device.

5. The method of claim 1, further comprising the following steps:

measuring a total power for every rotation of the pedals;

determining an average power by averaging the power measurements for a number of rotations of the pedals; and reporting the average power on the computer display of the portable electronic device.

6. A sensor system for monitoring a person performing a physical activity, the sensor system comprising:

a pair of sensor insoles, each having substrate layer shaped to be worn in a shoe and adjacent the underside of the person's feet, each of the substrate layers having a plurality of force sensors, an accelerometer, a transmitter for transmitting data from the plurality of force sensors and the accelerometer, and a battery operably connected to a printed circuit board having a computer processor and a computer memory; and a monitoring application software adapted to be operably installed in a computer memory of a portable electronic device for performing the following steps:

generating a digital model of the person;

displaying the digital model on the computer display of the portable electronic device;

displaying movement of the digital model, in real time, based upon the data received from the sensor insoles, so that the digital model of the person approximates the movement of the person performing the physical activity; and transmitting the digital model in real time via a network to a remote computer for display and analysis.

7. The sensor system of claim 6, wherein the monitoring application software is able to perform the following additional steps:

comparing the movement of the digital model with a preferred movement model;

determining if the actual movement of the person approximates the preferred movement model, or if correction is needed;

communicating with the person, in real time, with corrective instructions when correction is needed.

8. The sensor system of claim 6, wherein the monitoring application software is able to provide instructions on how to perform an exercise that are synchronized with the action exercise being performed.

* * * * *